US009474658B2

(12) United States Patent
Thorson et al.

(10) Patent No.: US 9,474,658 B2
(45) Date of Patent: Oct. 25, 2016

(54) METHOD OF MAKING DISPOSABLE PANTS HAVING UNDERWEAR-LIKE WAISTBANDS, AND PANT MADE THEREBY

(71) Applicant: Kimberly-Clark Worldwide, Inc., Neenah, WI (US)

(72) Inventors: Russell Evan Thorson, Appleton, WI (US); Todd W. Wilkes, Appleton, WI (US); Jesus S. Banda, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 481 days.

(21) Appl. No.: 14/158,930

(22) Filed: Jan. 20, 2014

(65) Prior Publication Data

US 2014/0135727 A1    May 15, 2014

Related U.S. Application Data

(62) Division of application No. 12/624,751, filed on Nov. 24, 2009, now Pat. No. 8,663,415.

(51) Int. Cl.
| | | |
|---|---|---|
| A61F 13/00 | (2006.01) | |
| B32B 38/00 | (2006.01) | |
| A61F 13/49 | (2006.01) | |
| A61F 13/15 | (2006.01) | |
| A61F 13/496 | (2006.01) | |
| B32B 38/10 | (2006.01) | |

(52) U.S. Cl.
CPC ... *A61F 13/49012* (2013.01); *A61F 13/00987* (2013.01); *A61F 13/15593* (2013.01); *A61F 13/15739* (2013.01); *A61F 13/15804* (2013.01); *A61F 13/49011* (2013.01); *A61F 13/4963* (2013.01); *B32B 38/10* (2013.01); *B32B 2555/02* (2013.01); *Y10T 156/1062* (2015.01)

(58) Field of Classification Search
CPC .. A61F 13/00; A61F 13/49; A61F 13/49012; A61F 13/00987; A61F 13/15; A61F 13/15739; A61F 13/15804; A61F 13/49011; A61F 13/4963; B32B 38/00; B32B 38/10
See application file for complete search history.

(56) References Cited

U.S. PATENT DOCUMENTS

| | | | |
|---|---|---|---|
| 5,163,932 | A | 11/1992 | Nomura et al. |
| 5,531,732 | A | 7/1996 | Wood |

(Continued)

FOREIGN PATENT DOCUMENTS

| | | |
|---|---|---|
| EP | 0 865 780 B1 | 2/2003 |
| JP | 10-337300 A | 12/1998 |

(Continued)

*Primary Examiner* — Michael N Orlando
*Assistant Examiner* — Matthew Hoover
(74) *Attorney, Agent, or Firm* — Kimberly-Clark Worldwide, Inc.

(57) ABSTRACT

A method of manufacturing disposable absorbent garments and a garment made thereby. In particular embodiments, the method comprises removing notches or holes of a garment web or webs adjacent to front and back waist edges to define a series of spaced apart front and back waist edge openings. The method includes providing front and back elastic waistband webs, and positioning the respective waistband webs to overlay at least a portion of each opening, and bonding the waistband webs to each other. The garment includes first and second waist edge cutouts, wherein two side seams extend from the waist edge cutouts to respective leg openings. The garment further includes front and back elastic waistbands attached to each other at first and second waistband side seams.

23 Claims, 20 Drawing Sheets

(56) References Cited

U.S. PATENT DOCUMENTS

| | | | |
|---|---|---|---|
| 5,693,038 A | 12/1997 | Suzuki et al. | |
| 5,746,731 A * | 5/1998 | Hisada | A61F 13/49 450/154 |
| 6,475,201 B2 * | 11/2002 | Saito | A41B 9/001 2/400 |
| 6,514,233 B1 | 2/2003 | Glaug | |
| 7,255,688 B2 | 8/2007 | Sasaki et al. | |
| 2003/0084984 A1 | 5/2003 | Glaug et al. | |
| 2003/0130641 A1 | 7/2003 | Richlen et al. | |
| 2003/0217407 A1 | 11/2003 | Andrews-Jones | |
| 2004/0060648 A1 | 4/2004 | Thorson et al. | |
| 2005/0010188 A1 | 1/2005 | Glaug et al. | |
| 2005/0175269 A1 | 8/2005 | Ashton et al. | |
| 2006/0108054 A1 * | 5/2006 | Ukegawa | A61F 13/15699 156/160 |
| 2006/0264858 A1 | 11/2006 | Roe et al. | |
| 2008/0051755 A1 | 2/2008 | Otsubo | |
| 2008/0108963 A1 | 5/2008 | Ashton et al. | |
| 2009/0036860 A1 | 2/2009 | Sugiyama et al. | |
| 2010/0004616 A1 | 1/2010 | Nakamura et al. | |
| 2010/0038018 A1 | 2/2010 | Otsubo | |
| 2012/0283683 A1 | 11/2012 | Tai et al. | |

FOREIGN PATENT DOCUMENTS

| | | |
|---|---|---|
| JP | 11-104180 A | 4/1999 |
| JP | 2003-247101 A | 9/2003 |
| JP | 2004-136050 A | 5/2004 |
| WO | WO 98/13002 A1 | 4/1998 |
| WO | WO 2006/071144 A1 | 7/2006 |

* cited by examiner

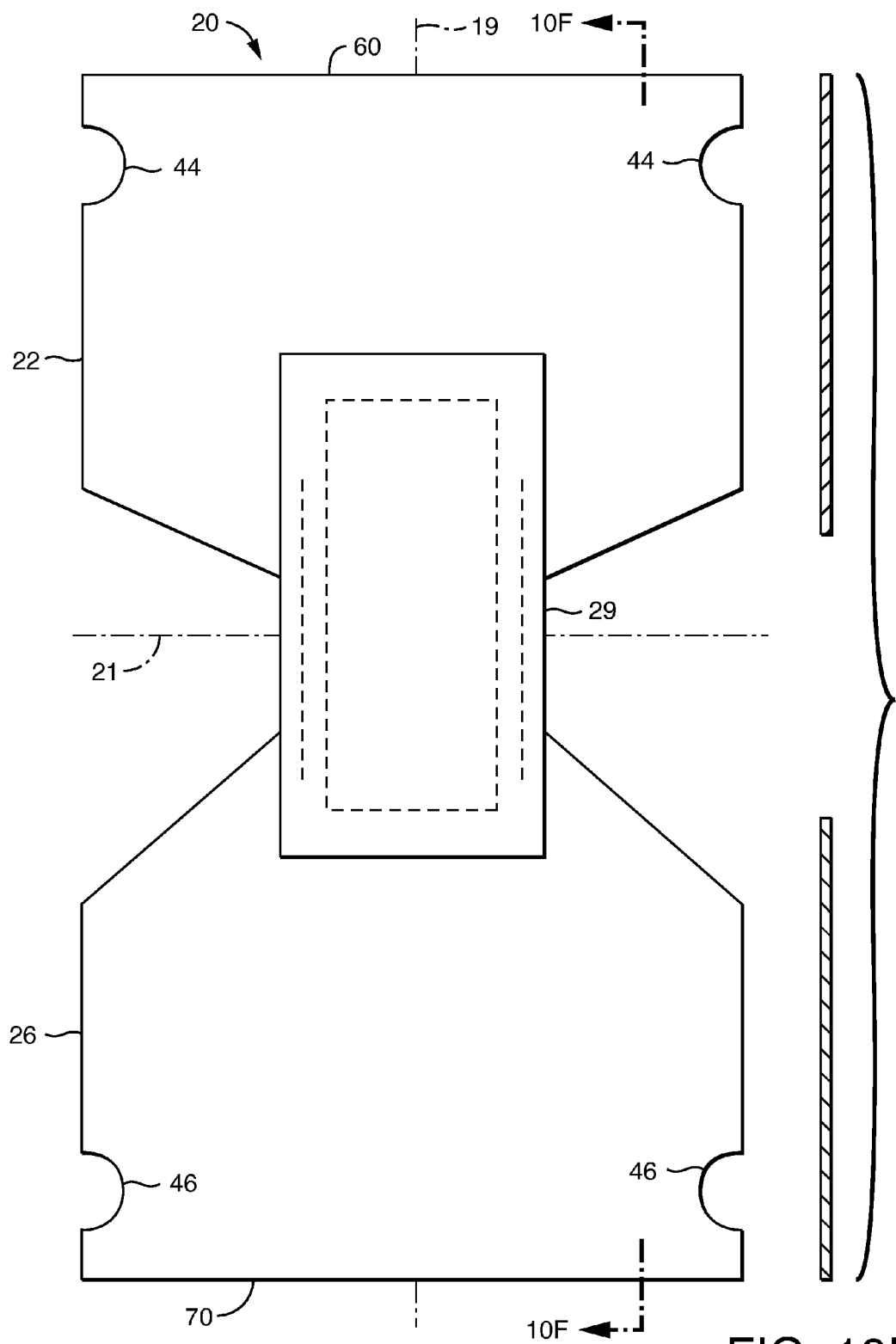

METHOD OF MAKING DISPOSABLE PANTS HAVING UNDERWEAR-LIKE WAISTBANDS, AND PANT MADE THEREBY

This application is a divisional of prior application Ser. No. 12/624,751 filed on Nov. 24, 2009. The entirety of application Ser. No. 12/624,751 is hereby incorporated by reference.

BACKGROUND

Pant-like disposable garments are in common use in today's society. For example, disposable absorbent underwear for incontinence and enuresis conditions, disposable training pants, and disposable menstrual panties are common in the marketplace. It is desirable to make such products as much like normal cloth underwear as possible. For example, wearers of incontinence and enuresis garments generally wish to conceal the fact that they are wearing such products, and therefore desire the garments to resemble normal cloth underwear as closely as possible. In another example, children wearing toilet training pants take pride in the fact that they are no longer wearing diapers, and providing them with a disposable training pant product that closely resembles real underwear supports this process. It is also important that such garments provide a snug and secure fit, both to provide comfort to the wearer and to minimize leakage of bodily waste out of the absorbent garment. For example, it is common for many products to include waistbands or leg bands, often elasticized, to provide improved fit, leakage management, and underwear-like aesthetics.

However, creating underwear-like waistbands on disposable garments can be problematic at commercial manufacturing speeds. For example, one conventional disposable pant design employs front and back elastomeric body panels, with a separate elastic waistband attached thereto. Another design employs an integral waistband in which portions of the front and back body panels are folded over and sandwich elastic elements to create the waistband. In both cases, the front panel and back panels are joined together along bonded side seams, commonly via the use of ultrasonic, heat, and/or pressure bonding. In certain regions of the front and back body panels where the waistband resides, the seaming mechanism (e.g., an ultrasonic, heat, and/or pressure bonder) must penetrate not only the waistband materials but the front and back body panel materials as well. In contrast, in the regions of the front and back body panels where the waistband is not present, the seaming mechanism usually must only penetrate the front and back body panel materials to complete the seam. To reduce manufacturing equipment complexity and cost, it is common to use a single seaming mechanism to create an entire side seam, even though such entire side seam extends both through regions where a waistband is present, and regions where no waistband is present. As a result, the single seaming mechanism must be engineered to penetrate both regions adequately, but not in a way that damages either portion.

For example, in a garment in which the front and back body panels are each constructed of an elastomeric film laminate, in which an elastomeric film layer is sandwiched between two nonwoven layers, joining the front panel to the back panel via a pair of side seams requires that the seaming mechanism (e.g., an ultrasonic, heat, and/or pressure bonder) penetrate six layers of material (three layers of the front panel laminate, and three layers of the back panel laminate). If this garment also employs an additional waistband layer constructed of a similar laminate material (whether separately attached or integrally folded), joining the front panel to the back panel in those regions where the waistband is present requires that the seaming mechanism penetrate twelve layers of material (three layers of the front panel laminate, three layers of the back panel laminate, three layers of the front waistband, and three layers of the back waistband). As noted above, as it is common to employ a single seaming operation to create each seam in its entirety, the seaming mechanism in such conventional designs must be aggressive enough to seam the relatively high number of layers in the waistband region, but not so aggressive that the material in the non-waistband regions of the seam becomes damaged, perforated, or burned.

At modest manufacturing speeds, this dilemma can be adequately managed. However, at higher speeds of manufacture, it becomes increasingly difficult to engineer a seaming mechanism to bond both the waistband region and the non-waistband region without encountering the problems mentioned above. Therefore, what is needed is a method of making disposable pant-like garments having waistbands that can help avoid this circumstance.

SUMMARY OF THE INVENTION

To meet the above-described unmet needs in the art, a new process for making pant-like disposable garments, and a garment made thereby, have been invented.

In one embodiment of the method aspect of the invention, a method of manufacturing a plurality of disposable absorbent garments comprises providing a garment web traveling in a machine direction, the garment web having a front region defining a front waist edge and a back region defining a back waist edge, both the front waist edge and the back waist edge extending in the machine direction. The method further comprises removing portions of the garment web adjacent to the front waist edge to define a series of spaced apart front waist edge openings. The method further comprises removing portions of the garment web adjacent to the back waist edge to define a series of spaced apart back waist edge openings. The method further comprises removing central portions of the garment web to define a series of spaced apart leg opening holes. The method further comprises providing a front elastic waistband web and a back elastic waistband web; positioning the front elastic waistband web proximate the front waist edge such that the front elastic waistband web overlays at least a portion of each front waist edge opening; and positioning the back elastic waistband web proximate the back waist edge such that the back elastic waistband web overlays at least a portion of each back waist edge opening. The method further comprises providing a supply of individual absorbent assemblies, superposing individual absorbent assemblies over the garment web, and attaching the individual absorbent assemblies to the garment web. The method further comprises folding the garment web along a centerline that extends in the machine direction, such that the front waist edge is brought into close proximity with the back waist edge. The method further comprises attaching the front region to the back region to create a series of garment side seam bonds spaced apart in the machine direction. The method further comprises attaching the front elastic waistband web to the back elastic waistband web to create a series of waistband side seam bonds spaced apart in the machine direction. The method further comprises cutting the garment web and the elastic waistband webs at a series of cut locations spaced apart in the machine direction to create the plurality of disposable absorbent garments.

In another embodiment of the method aspect of the present invention, a method of manufacturing a plurality of disposable absorbent garments comprises providing a front panel web traveling in a machine direction, the front panel web defining a front waist edge extending in the machine direction. The method further comprises providing a back panel web traveling in the machine direction, the back panel web defining a back waist edge extending in the machine direction. The method further comprises removing portions of the front panel web adjacent to the front waist edge to define a series of spaced apart front waist edge openings. The method further comprises removing portions of the back panel web adjacent to the back waist edge to define a series of spaced apart back waist edge openings. The method further comprises providing a front elastic waistband web and a back elastic waistband web; positioning the front elastic waistband web proximate the front waist edge such that the front elastic waistband web overlays at least a portion of each front waist edge opening; and positioning the back elastic waistband web proximate the back waist edge such that the back elastic waistband web overlays at least a portion of each back waist edge opening. The method further comprises providing a supply of individual absorbent assemblies, each individual absorbent assembly having a front end and a back end, and attaching the front end of each individual absorbent assembly to the front panel web and attaching the back end of each individual absorbent assembly to the back panel web to create a composite garment web such that each individual absorbent assembly extends laterally between and interconnects the front panel web to the back panel web. The method further comprises folding the composite garment web along a central fold line that extends in the machine direction, such that the front waist edge is brought into close proximity with the back waist edge. The method further comprises attaching the front panel web to the back panel web to create a series of garment side seam bonds spaced apart in the machine direction. The method further comprises attaching the front elastic waistband web to the back elastic waistband web to create a series of waistband side seam bonds spaced apart in the machine direction. The method further comprises cutting the garment web and the elastic waistband webs at a series of cut locations spaced apart in the machine direction to create the plurality of disposable absorbent garments.

In one embodiment of the garment aspect of the present inventions, a disposable absorbent garment comprises a front panel defining a front waist edge and a back panel defining a back waist edge. The garment further comprises a crotch panel extending longitudinally between and connecting the front panel and the back panel. The garment further comprises first and second transversely opposite side seams connecting the front panel to the back panel, and further define first and second leg openings and a waist opening. The garment further comprises first and second waist edge cutouts, wherein the first side seam extends from the first leg opening to the first waist edge cutout, and wherein the second side seam extends from the second leg opening to the second waist edge cutout. The garment further comprises a front elastic waistband and a back elastic waistband, wherein the front elastic waistband is attached to the back elastic waistband at first and second waistband side seams. At least a portion of the first waistband side seam overlays at least a portion of the first waist edge cutout, and at least a portion of the second waistband side seam overlays at least a portion of the second waist edge cutout. In particular embodiments, the front elastic waistband is substantially unattached to the front panel along a majority of the front elastic waistband width, and the back elastic waistband is substantially unattached to the back panel along a majority of the back elastic waistband width.

DEFINITIONS

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least percent of its relaxed length and which will recover, upon release of the applied force, at least 20 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

"Member" when used in the singular can have the dual meaning of a single element or a plurality of elements.

These terms may be defined with additional language in the remaining portions of the specification.

BRIEF DESCRIPTION OF THE DRAWINGS

FIG. 10E depicts the garment of FIG. 10A but with the waistbands in an outwardly folded configuration.

FIG. 10F is a cross-sectional view of the article of FIG. 10E as viewed along line 10E-10F.

DETAILED DESCRIPTION OF EXEMPLARY EMBODIMENTS

Figure 1:
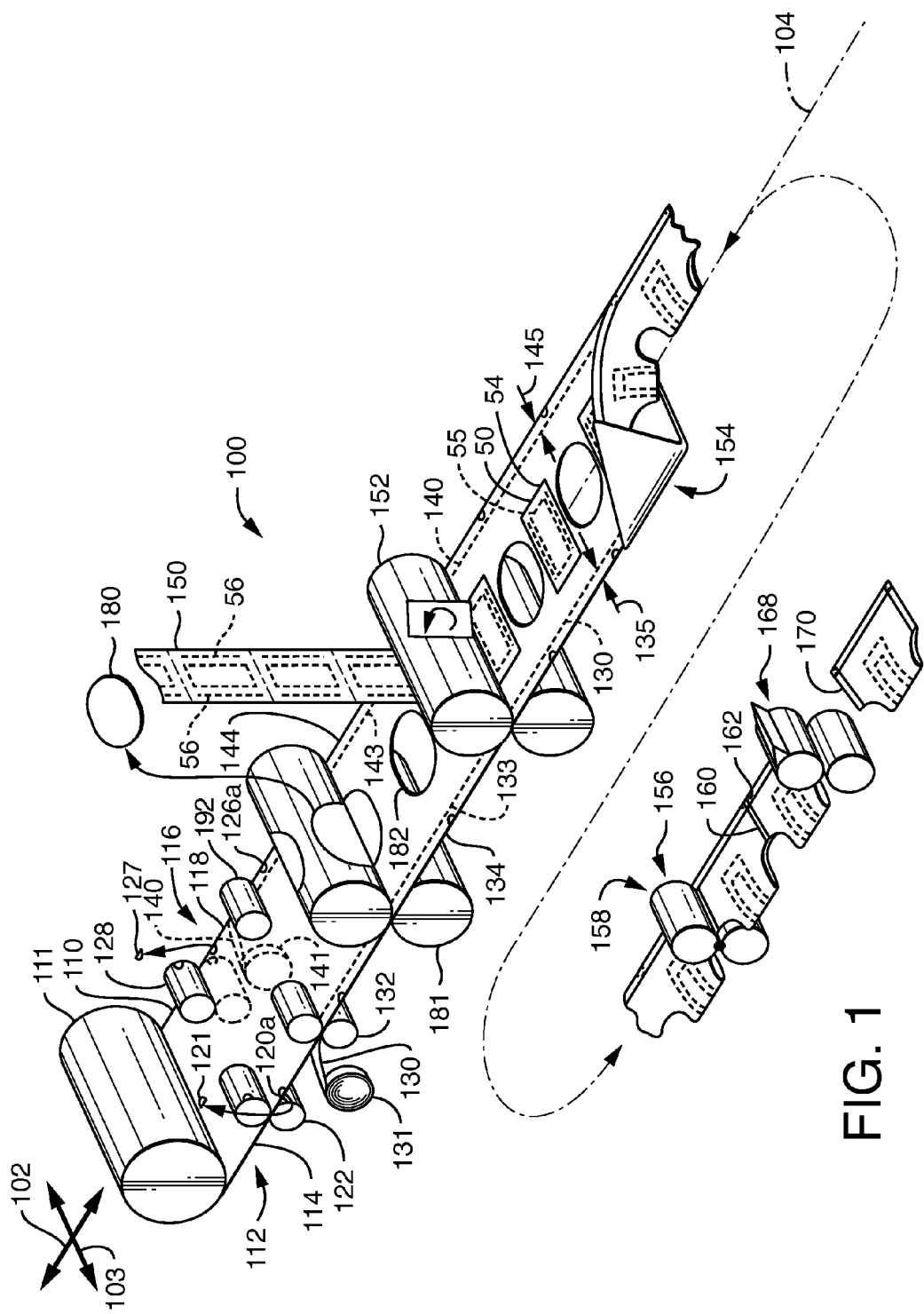
FIG. 1 representatively illustrates a perspective view of one embodiment of a manufacturing process incorporating principles of the method aspect of the present invention.

Reference to FIGS. 1-10 shall be made in describing various aspects and embodiments of the invention. It should be noted that the embodiments depicted in FIGS. 1-10 are merely representative examples of the garment and process aspects of the invention. Although for illustrative purposes certain features of the present invention shall be described and illustrated with respect to an adult incontinence garment and process for making such garment, the various aspects and embodiments of the present invention are also suitable for use with disposable diapers, disposable swim pants, disposable training pants, disposable enuresis garments, and the like. As representatively illustrated in FIGS. 1-8, the invention in one aspect relates to a method 100 of manufacturing disposable pants. The method defines a machine or longitudinal direction 102 and a cross-machine or lateral direction 103. In particular embodiments, such as those representatively illustrated in FIGS. 1-4, the method includes providing a garment web 110 traveling in the machine direction 102. The garment web defines a front region 112 defining a front waist edge 114 and a back region 116 defining a back waist edge 118. Both the front waist edge 114 and the back waist edge 118 extend in the machine direction 102. In particular embodiments, the garment web is provided via a garment web supply roll 111. The garment web may comprise a nonwoven material. The garment web could comprise, for example, an elastomeric film laminate, such as one comprising an elastic film core layer sandwiched between two nonwoven facing layers, a material which is common to those of skill in the art. U.S. Patent Application Publications US 2008/0095978 and US 2009/0197041, both assigned to Kimberly-Clark Worldwide, Inc., provide examples of technology suitable for use in creating the front and back body panel elastomeric film laminates, although other elastomeric film laminates can also be used.

Figure 4:
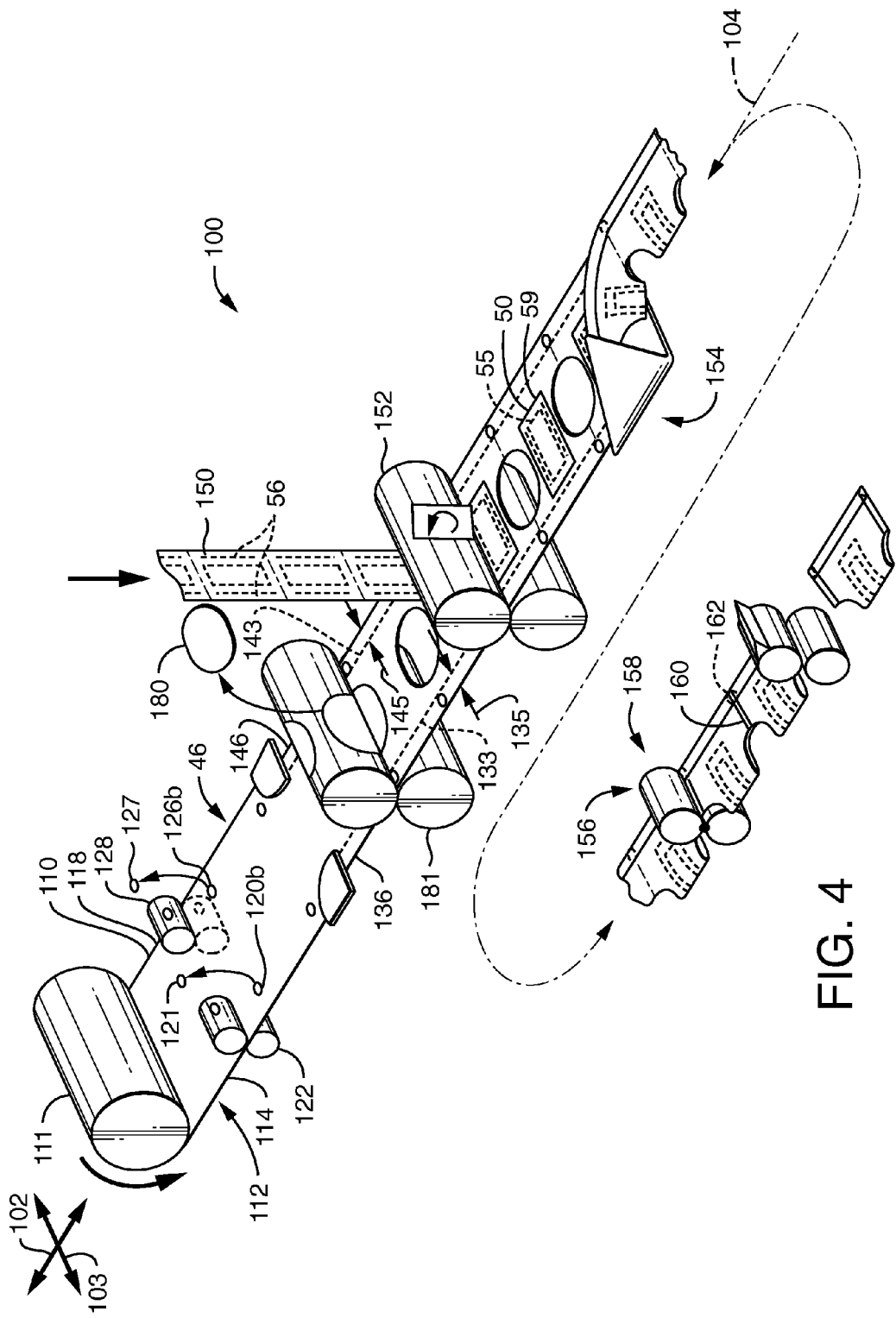
FIG. 4 representatively illustrates a perspective view of an alternative embodiment of a manufacturing process incorporating principles of the method aspect of the present invention.

The method further includes removing portions 121 of the garment web 110 adjacent to the front waist edge 114, such as via a cutter unit 122, to define a series of spaced apart front waist edge openings 120. The method further includes removing portions 127 of the garment web 110 adjacent to the back waist edge 118, such as via a cutter unit 128, to define a series of spaced apart back waist edge openings 126. The openings 120 and 126 can be notches or holes. "Notch" as used herein means an opening along the edge of a substrate or garment such that it is only partially enclosed by surrounding material. The openings 120a and 126a of FIGS. 1-3 and 5-7 are illustrative examples of notches. "Hole" as used herein means an opening positioned entirely within the edges of a substrate or garment such that it is fully enclosed in two dimensions by surrounding material. The openings 120b and 126b of FIGS. 4 and 8 are illustrative examples of holes. Accordingly, in particular embodiments of the method, such as those representatively illustrated in FIGS. 1-3 and 5-7, each front waist edge opening comprises a front waist edge notch 120a, and each back waist edge opening comprises a back waist edge notch 126a. In other embodiments, such as those representatively illustrated in FIGS. 4 and 8, each front waist edge opening comprises a front waist edge hole 120b, and each back waist edge opening comprises a back waist edge hole 126b.

The method further includes removing central portions 180 of the garment web 110 to define a series of spaced apart leg opening holes 182, such as via cutter unit 181. The leg opening holes 182 present in the garment web 110 will, in the present embodiment, define portions of the leg openings in the finished garments.

The method 100 further includes providing a front elastic waistband web 130 and a back elastic waistband web 140, such as via roll supplies 131 and 141 respectively. The method further includes positioning the front elastic waistband web 130 proximate the front waist edge 114 such that the front elastic waistband web 130 overlays at least a portion of each front waist edge opening 120. The method further includes positioning the back elastic waistband web 140 proximate the back waist edge 118 such that the back elastic waistband web 140 overlays at least a portion of each back waist edge opening 118. For example, as representatively illustrated in FIGS. 1-3, the front elastic waistband 130 is positioned atop and connected to the garment web 110 along the front waist edge 114 (at front waistband attachment station 132) such that it at least partially covers, or completely covers, the front waist edge notch 120a, and the back elastic waistband 140 is positioned atop and connected to the garment web 110 (at back waistband attachment station 142) along the back waist edge 118 such that it at least partially covers, or completely covers, the back waist edge notch 126a. In an alternative example, representatively illustrated in FIG. 4, the front elastic waistband 130 is positioned atop and connected to the garment web 110 proximate the front waist edge 114 such that it at least partially covers, or complete covers, the front waist edge hole 120b, and the back elastic waistband web 140 is positioned atop and connected to the garment web 110 proximate the back waist edge 118 such that the back elastic waistband web 140 overlays at least a portion of each back waist edge hole 126b. The method can further include waist elastic strands affixed to the front and/or back waistband webs to impart elasticity thereto (not shown). For example, the waistband webs can be inherently elastomeric, or can be inherently non-elastomeric but made to be elastomeric by affixing elastic strands thereto.

Each front elastic waistband web 130 defines a front waistband web proximal edge 133 and a front waistband web distal edge 134, the front waistband web distal edge 134 being laterally outward of the front waistband web proximal edge 133. In particular embodiments of the method, the front elastic waistband web 130 is positioned so that the front waistband web distal edge 134 is substantially flush with the front waist edge 114. "Substantially flush" as used herein means flush but includes variation caused by normal manufacturing variation due to web weave (i.e., +/−6 millimeters). In another embodiment, the front elastic waistband web 130 is positioned so that the front waistband web distal edge 134 is positioned laterally outward of the front waist edge 114. "Laterally outward" as used herein means laterally away from a longitudinally extending centerline 104 of the garment web 110 or the longitudinally extending centerline of other process configurations (such as the centerline of two webs or the centerline of a composite garment web, as shall be described below in conjunction with alternative embodiments). In still another embodiment, the front elastic waistband web 130 is positioned so that the front waistband web distal edge 134 is positioned laterally inward of the front waist edge 114. "Laterally inward" as used herein means laterally toward a longitudinally extending centerline 104 of the garment web 110 or the longitudinally extending centerline of other process configurations. Similarly, each back elastic waistband web 140 defines a back waistband web proximal edge 143 and a back waistband web distal edge 144, the back waistband web distal edge 144 being laterally outward of the back waistband web proximal edge 143. In particular embodiments of the method, the back elastic waistband web 140 is positioned so that the back waistband web distal edge 144 is substantially flush with the back waist edge 118. In another embodiment, the back elastic waistband web 140 is positioned so that the back waistband web distal edge 144 is positioned laterally outward of the back waist edge 118. In still another embodiment, the back elastic waistband web 140 is positioned so that the back waistband web distal edge 144 is positioned laterally inward of the back waist edge 118.

In particular embodiments of the method, the front waistband web proximal edge 133 is substantially unattached to the garment web 110. "Substantially unattached" as used herein to describe a component or edge of a component means unattached along at least 90% of a web's length (in the machine direction). In addition or alternatively, the back waistband web proximal edge 143 is substantially unattached to the garment web 110. The garment resulting from such method embodiment is representatively illustrated in FIGS. 9A-9D, in which the front waistband web proximal edge 133 is unattached to the garment web. This optional configuration, in which one or both of the waistband web proximal edges are unattached to the garment web 110, can provide improved donning of the garment by providing a lip under which a wearer can place his or her fingertips to assist in pulling up the underwear-like garment. Many users of incontinence garments, such as young children and elderly individuals, have difficulty pulling up pant-style products. By leaving the proximal edge of the waistband web substantially unattached, users of the garment can, in certain embodiments of the present invention, use the proximal edge of the waistband as a handle to don the garment. For example, the front waistband web 130 in certain embodiments defines a laterally extending width 135, and the front waistband web 130 is substantially unattached to the garment web in the longitudinal direction 102 along a majority, and more preferably along at least 75%, of the front waistband web width 135. Similarly, the back waistband web 140 in certain embodiments defines a laterally extending width 145, and the back waistband web 140 is substantially unattached to the garment web 110 in the longitudinal direction 102 along a majority, and more preferably along at least 75%, of the back waistband web width 145.

In certain embodiments of the method and as representatively illustrated in FIG. 4, one or both of the waistband webs 130/140 is integral with the garment web 110. In such embodiments, providing the front elastic waistband web 130 comprises folding the garment web 110 laterally inward in the front region 112, thereby defining a front end fold 136. Similarly, providing the back elastic waistband web 140 comprises folding the garment web 110 laterally inward in the back region 116, thereby defining a back end fold 146. Each front elastic waistband web 130 defines a front waistband web proximal edge 133 positioned laterally inward of the front end fold 136, and each back elastic waistband web 140 defines a back waistband web proximal edge 143 positioned laterally inward of the back end fold 146. As with the embodiments described earlier, the method, in particular embodiments in which one or both of the waistband webs is integral with the garment web 110 (as representatively illustrated in FIG. 4), the front waistband web proximal edge 133 is substantially unattached to the garment web 110. In addition or alternatively, the back waistband web proximal edge 143 is substantially unattached to the garment web 110. The garment resulting from such method embodiment is representatively illustrated in FIGS. 10A-10E, in which the front waistband web proximal edge 133 is unattached to the garment web. This optional configuration, in which one or both of the waistband web proximal edges are unattached to the garment web 110, can provide improved donning of the garment as described above. For example, the front waistband web 130 in certain embodiments defines a laterally extending width 135, and the front waistband web 130 is substantially unattached to the garment web in the longitudinal direction 102 along a majority, and more preferably along at least 75%, of the front waistband web width 135. Similarly, the back waistband web 140 in certain embodiments defines a laterally extending width 145, and the back waistband web 140 is substantially unattached to the garment web 110 in the longitudinal direction 102 along a majority, and more preferably along at least 75%, of the back waistband web width 145.

The method further comprises providing a supply 150 of individual absorbent assemblies 50, superposing individual absorbent assemblies 50 over the garment web 110, and attaching the individual absorbent assemblies 50 to the garment web 110. The absorbent assemblies can be configured in any manner suitable for use in absorbent garments as is known in the art. For example, one optional configuration for the supply of absorbent assemblies includes a liquid permeable topsheet layer 54, a liquid impermeable backsheet layer, and a fluid absorbing core 55 sandwiched therebetween. Leg elastics 56 which run alongside the fluid absorbing core may be optionally included. Certain embodiments, such as those representatively illustrated in FIGS. 1-4, include cutting the individual absorbent assemblies 50 from the supply 150 and rotating them 90 degrees at a cut-and-rotate station 152.

The method further comprises folding the garment web 110 (such as at folding station 154) along a longitudinally extending centerline 104 that extends in the machine direction 102, such that the front waist edge 114 is brought into close proximity with the back waist edge 118. The method further includes attaching the front region 112 to the back region 116 (such as at seaming station 156) to create a series of garment side seam bonds 160 spaced apart in the machine direction 102. The method further includes attaching the front elastic waistband web 130 to the back elastic waistband web 140 (such as at seaming station 158) to create a series of waistband side seam bonds 162 spaced apart in the machine direction 102. Finally, the method includes cutting the garment web 110 and the elastic waistband webs 130/140 (such as at cutting station 168) at a series of cut locations 170 spaced apart in the machine direction 102 to create the plurality of disposable absorbent garments. The garment side seam bonds 160 and the waistband side seam bonds 162 can be formed at the same seaming station (as depicted) or at separate seaming stations. Additionally, either or both of the seaming operations can be performed along with the final cutting operation at a single station, or at separate stations (as depicted).

An alternative embodiment of the method aspect of the present invention, which incorporates many of the same techniques described above but which begins with two separate "garment" webs as opposed to a single garment web, shall now be described. In this alternative approach, exemplary embodiments of which are representatively illustrated in FIGS. 5-8, the method 100 includes providing a front panel web 113 traveling in a machine direction 102. The front panel web 113 defines a front waist edge 114 which extends in the machine direction. The method 100 further comprises providing a back panel web 117 traveling in the machine direction 102. The back panel web 117 defines a back waist edge 118 which also extends in the machine direction 102. Preferably, as representatively illustrated in FIGS. 5-8, the front panel web 113 is distinct from and spaced laterally apart from the back panel web 117. In particular embodiments, such as that representatively illustrated in FIGS. 5-8, the front panel web 113 is provided via a front panel web supply roll 115, and the back panel web 117 is provided via a back panel web supply roll 119. Alternatively, the front and back panel webs 113/117 may be provided by first providing a "parent" web or roll, and subsequently slitting the parent web along a generally longitudinally extending line, which may be straight or not straight, to provide the front panel web 113 and the back panel web 117. The front panel web and the back panel web may each comprise a nonwoven material. Each could comprise, for example, an elastomeric film laminate, such as elastic film core layer sandwiched between two nonwoven facing layers, a material which is common to those of skill in the art, and novel examples of which are discussed earlier.

The method in this embodiment further includes removing portions 121 of the front panel web 113 adjacent to the front waist edge 114, such as via a cutter unit 122, to define a series of spaced apart front waist edge openings 120. The method further includes removing portions 127 of the back panel web 117 adjacent to the back waist edge 118 to define a series of spaced apart back waist edge openings 126. The openings can be notches or holes as defined above. The method can optionally also include removing central portions 183 of the front panel web 113 and/or removing central portions 187 of the back panel web 117, such as via cutter unit 181, to define shaped front panel web leg edges 184 and/or shaped back leg edges 188.

Figure 5:
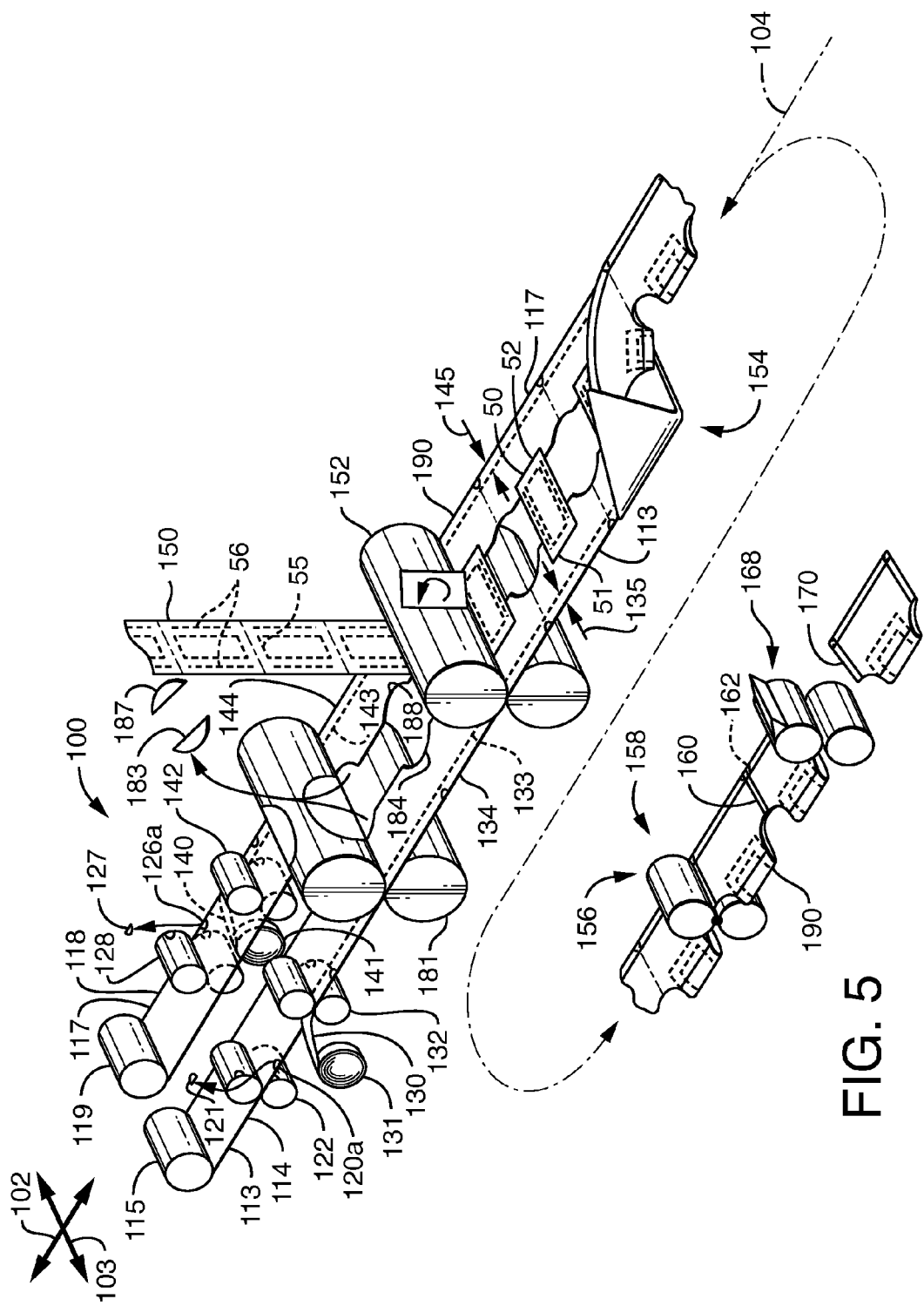
FIG. 5 representatively illustrates a perspective view of an alternative embodiment of a manufacturing process incorporating principles of the method aspect of the present invention.
Figure 6:
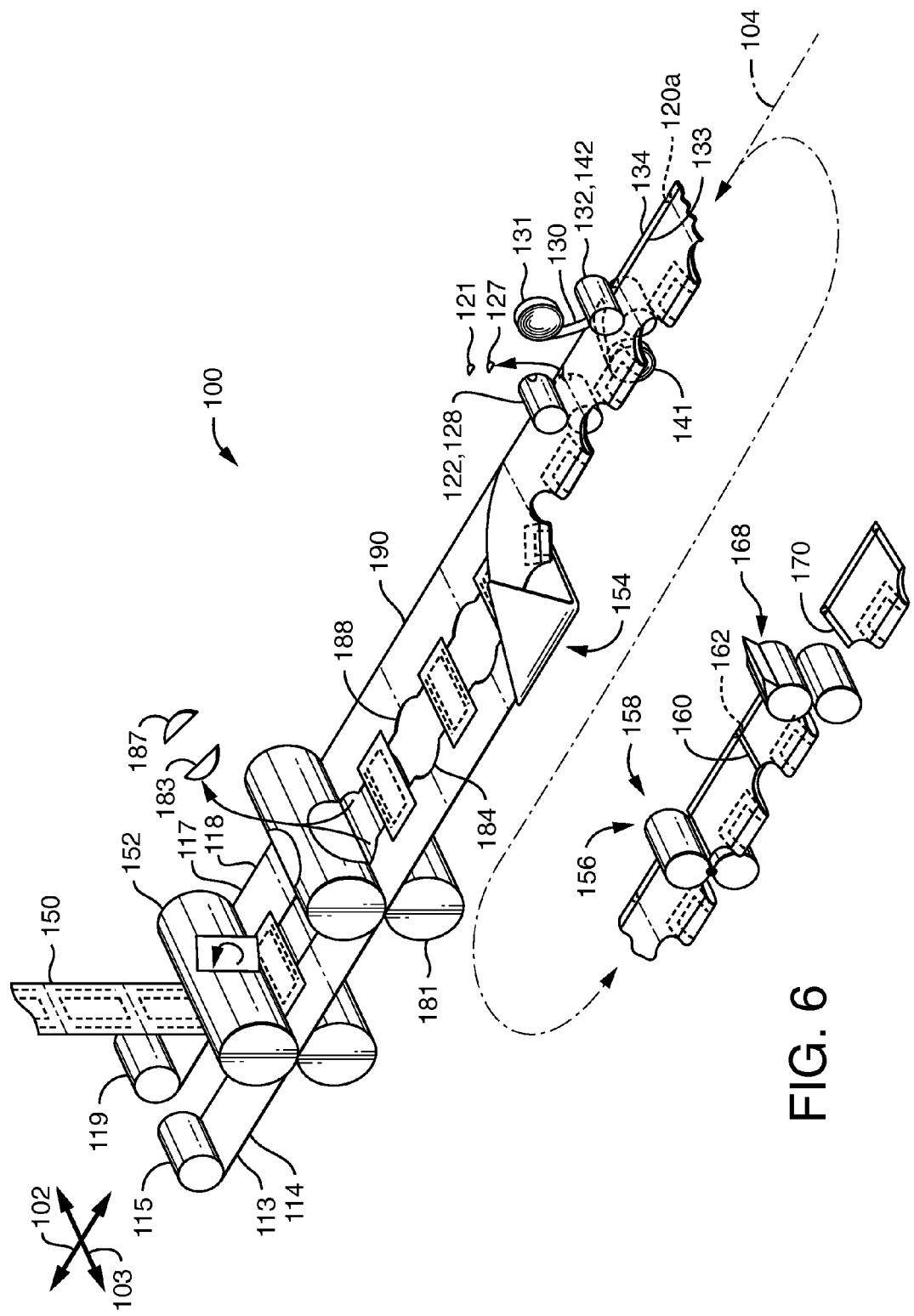
FIG. 6 representatively illustrates a perspective view of an alternative embodiment of a manufacturing process incorporating principles of the method aspect of the present invention.
Figure 7:
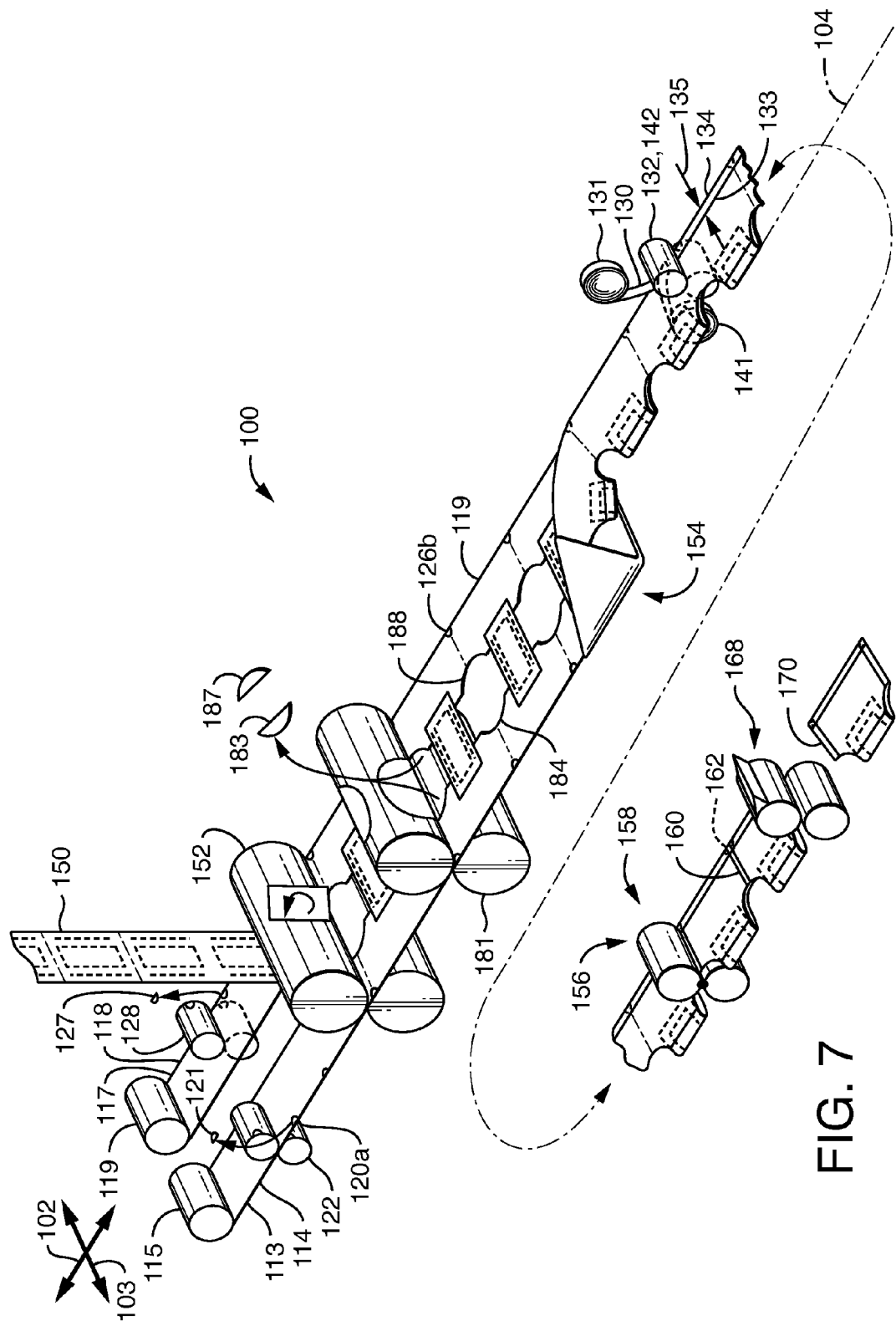
FIG. 7 representatively illustrates a perspective view of an alternative embodiment of a manufacturing process incorporating principles of the method aspect of the present invention.
Figure 8:
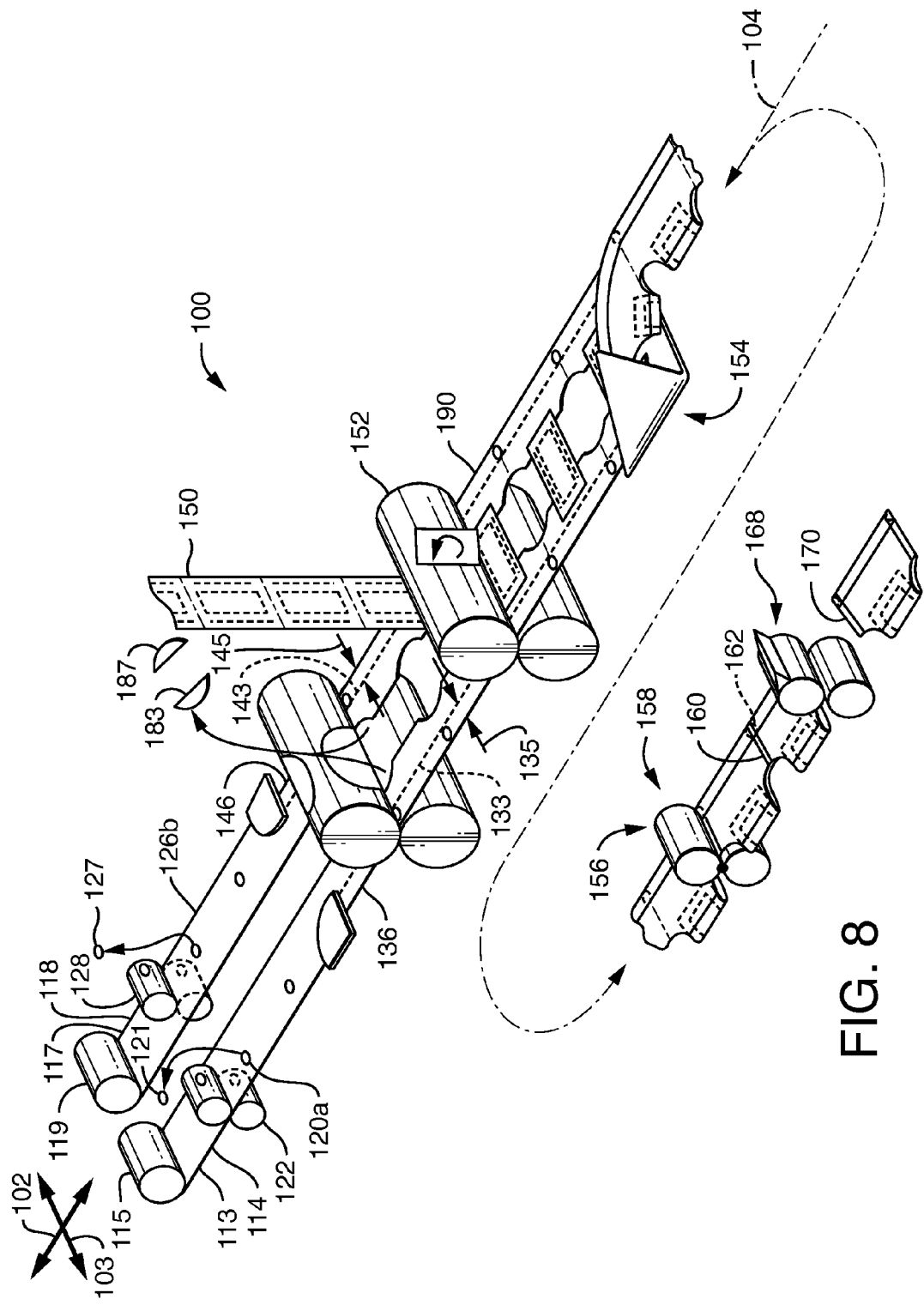
FIG. 8 representatively illustrates a perspective view of an alternative embodiment of a manufacturing process incorporating principles of the method aspect of the present invention.
Figures 9A, 9B:
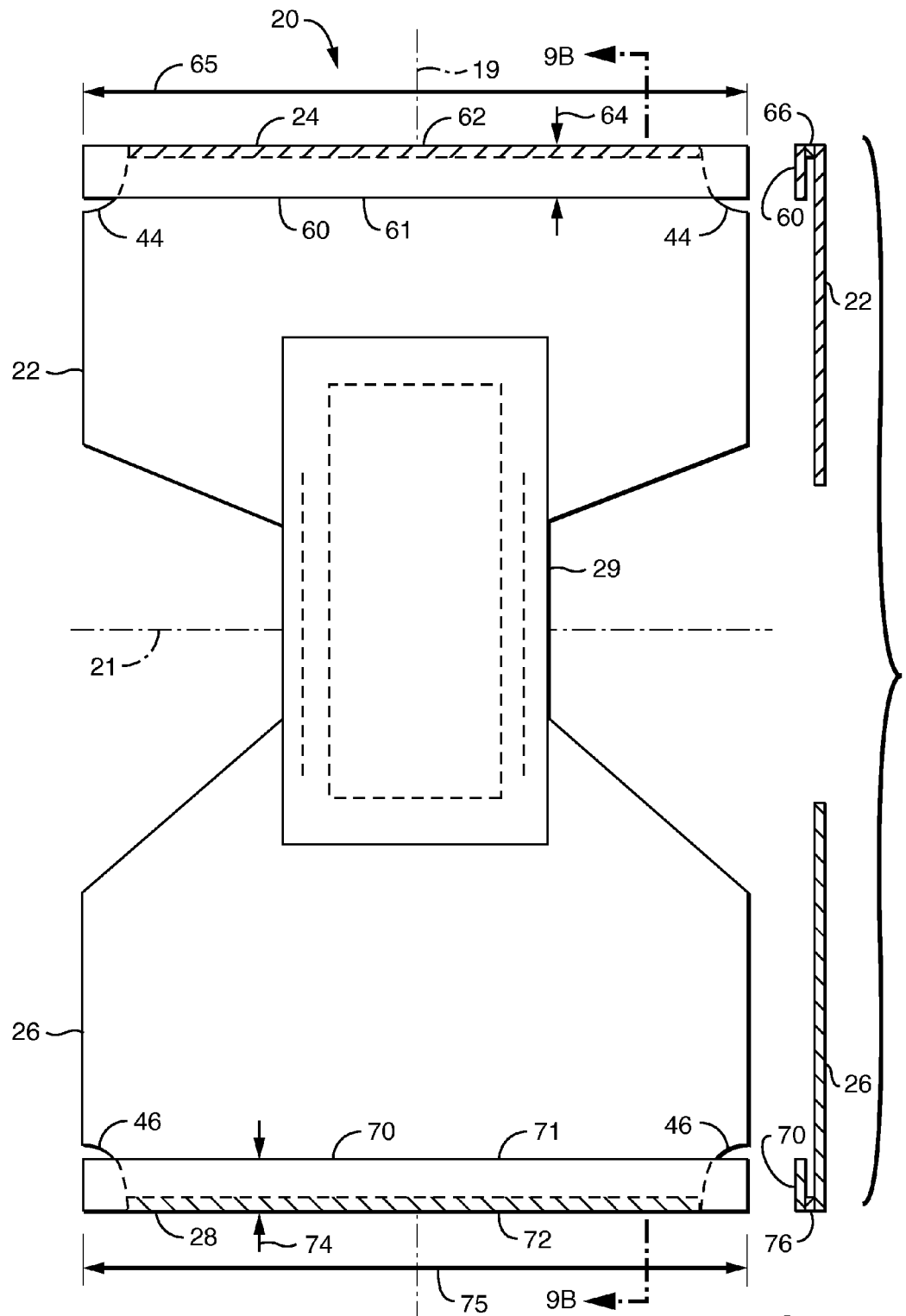
FIG. 9A representatively illustrates a plan view of a disposable absorbent garment incorporating principles of the garment aspect of the present invention, shown in a fully stretched and laid-flat condition, prior to the joining of the front and back waist regions, and showing the surface of the article that faces toward the wearer when the article is worn.
FIG. 9B is a cross-sectional view of the article of FIG. 9A as viewed along line 9B-9B.
Figure 9C:
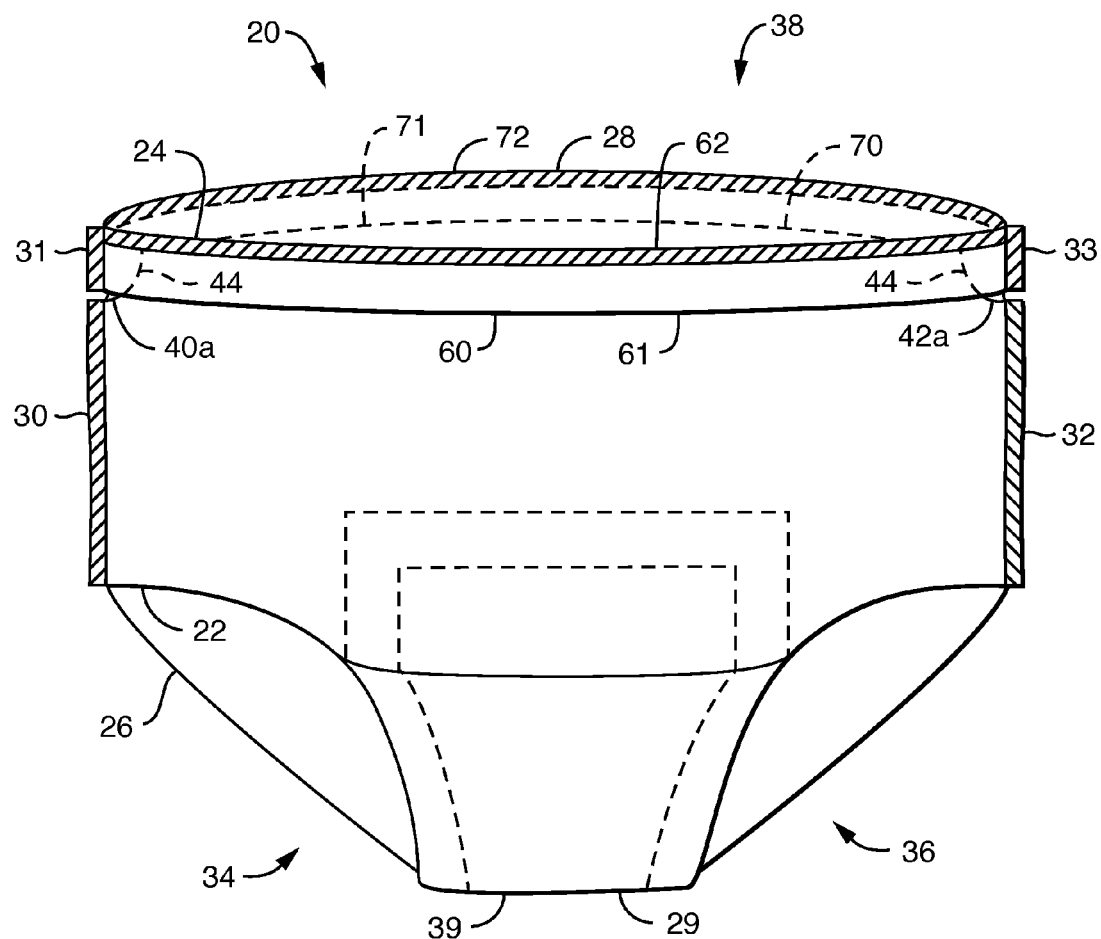
FIG. 9C is a front perspective view of the article of FIG. 9A, shown in a fully assembled condition.
Figure 9D:
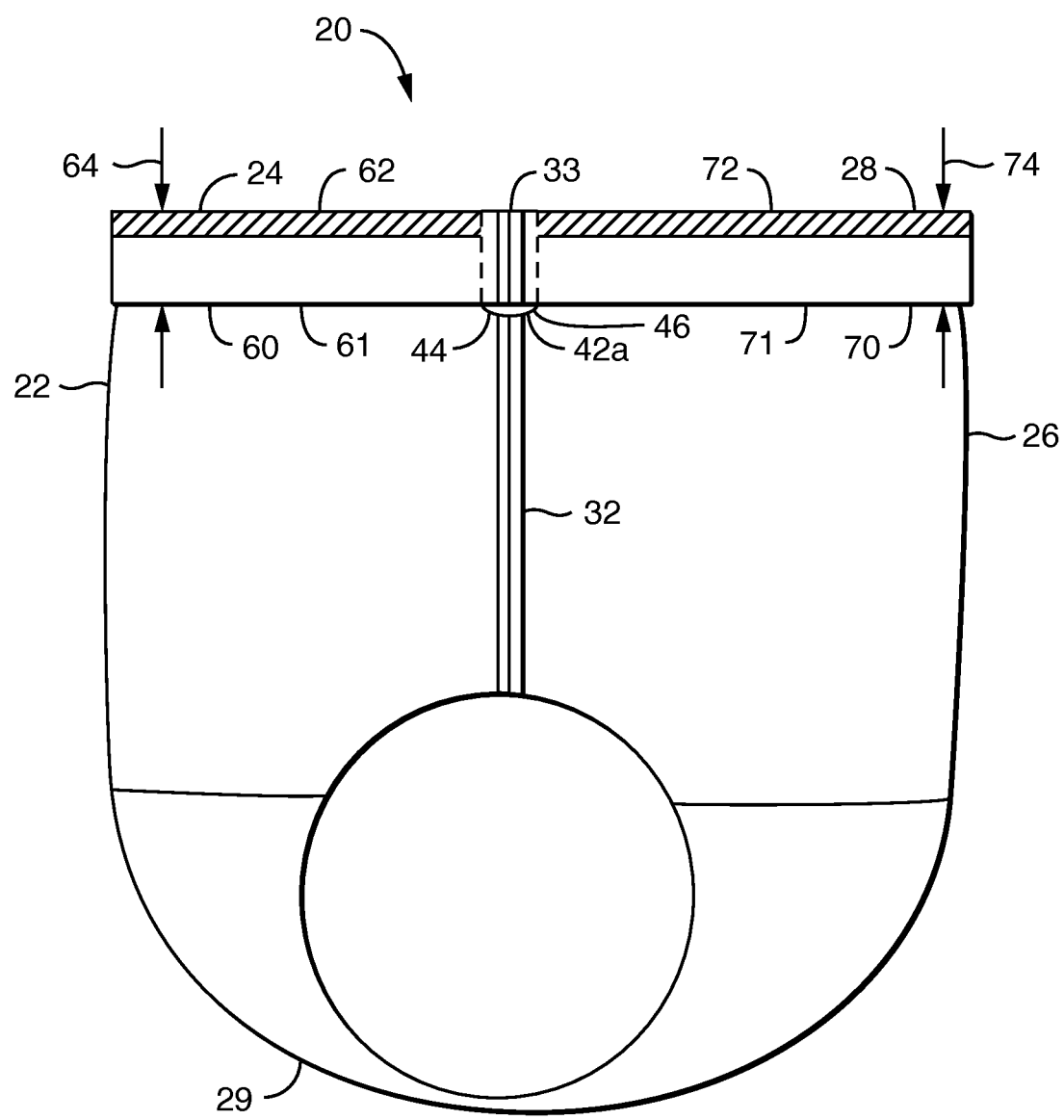
FIG. 9D is a side view of the article of FIG. 9C.
Figures 9E, 9F:
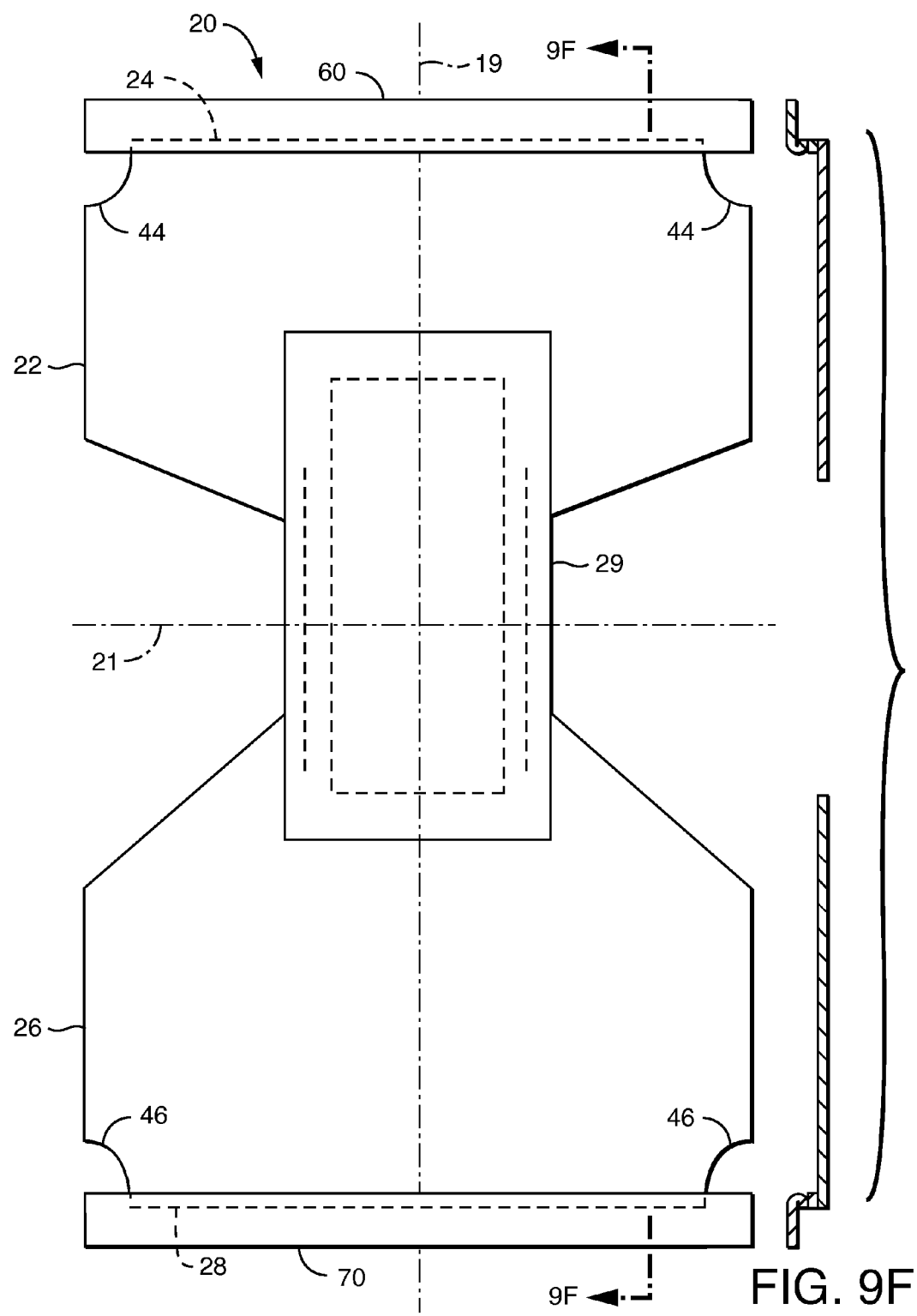
FIG. 9E depicts the garment of FIG. 9A but with the waistbands in an outwardly or upwardly folded configuration.
FIG. 9F is a cross-sectional view of the article of FIG. 9E as viewed along line 9F-9F.
Figure 9G:
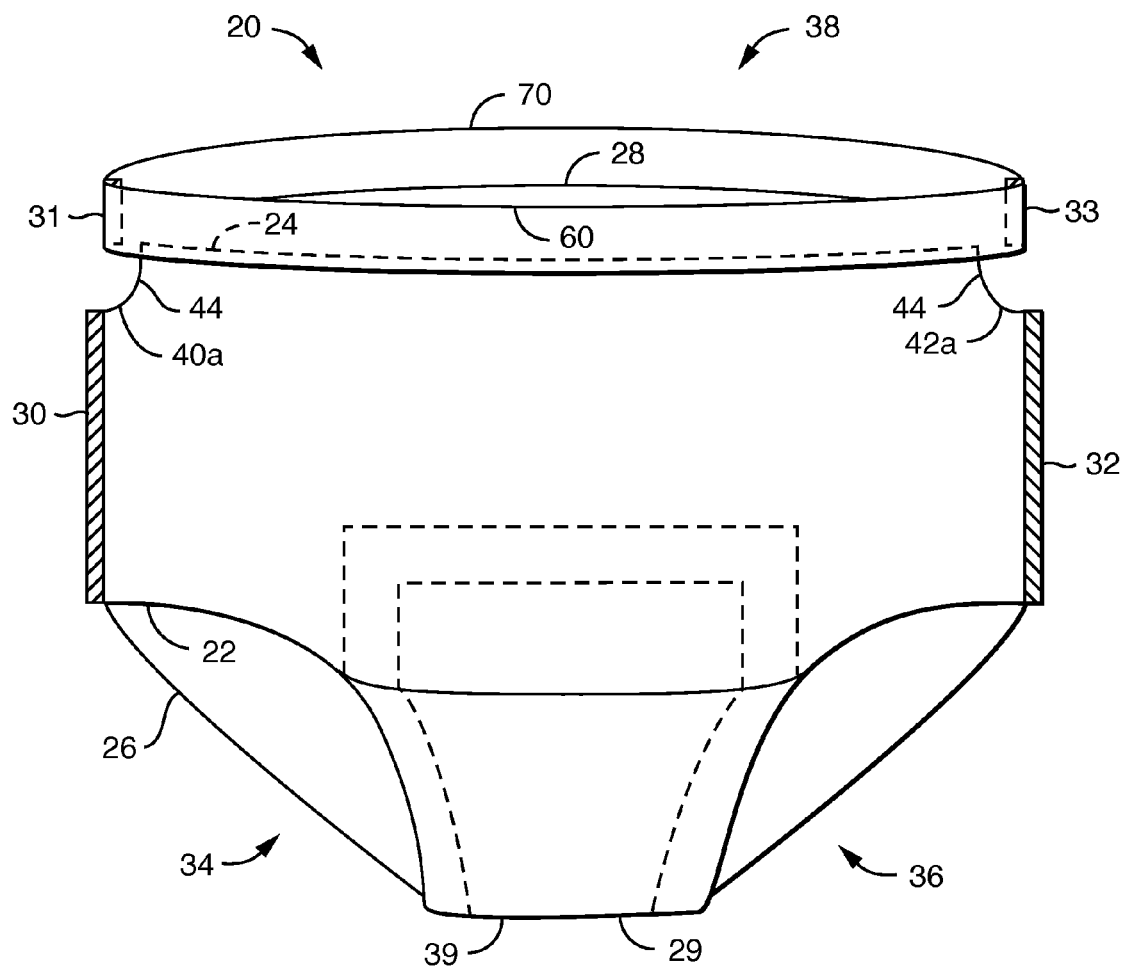
FIG. 9G is a front perspective view of the article of FIG. 9E, shown in a fully assembled condition.
Figure 9H:
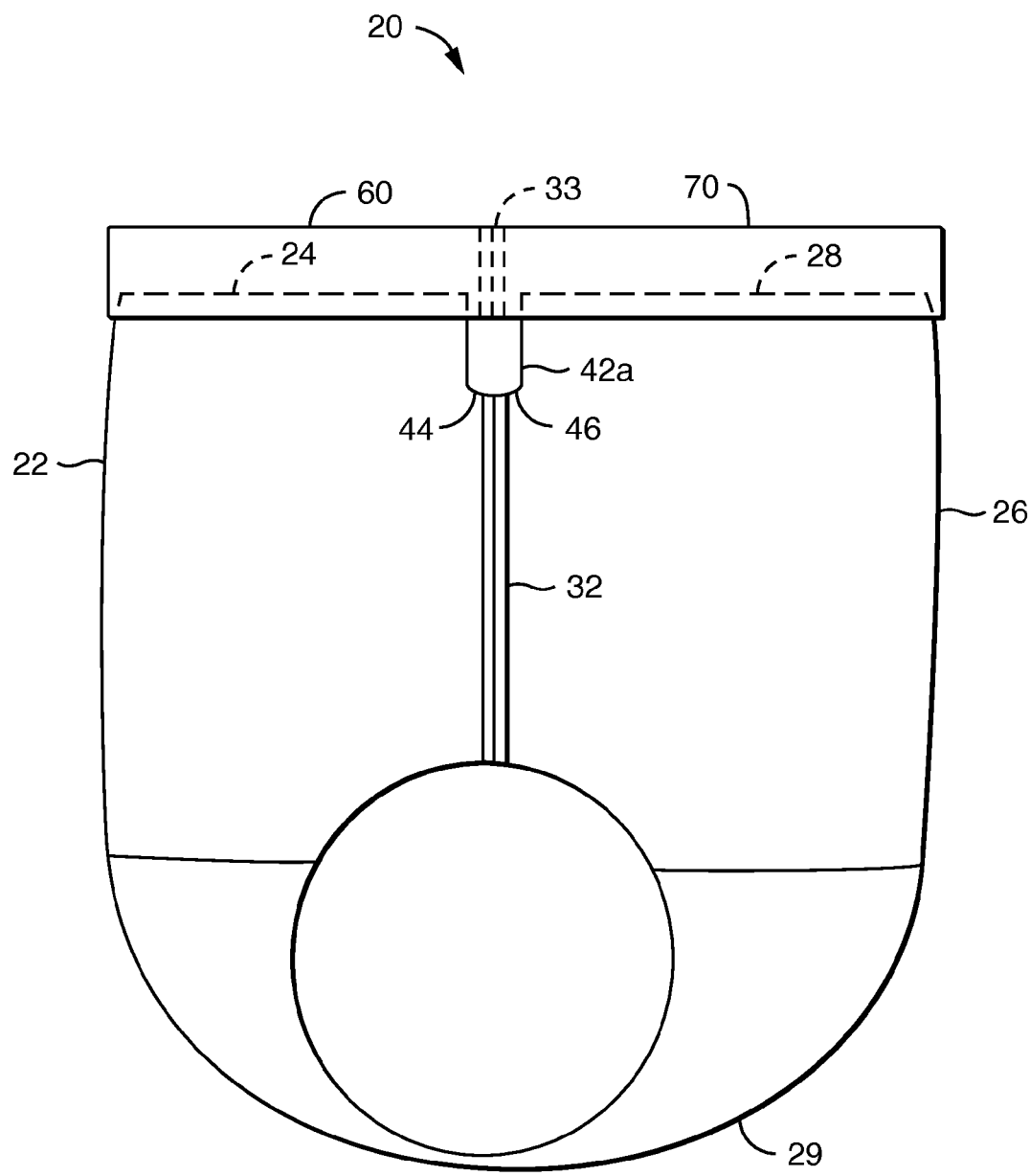
FIG. 9H is a side view of the article of FIG. 9G.
Figures 10A, 10B:
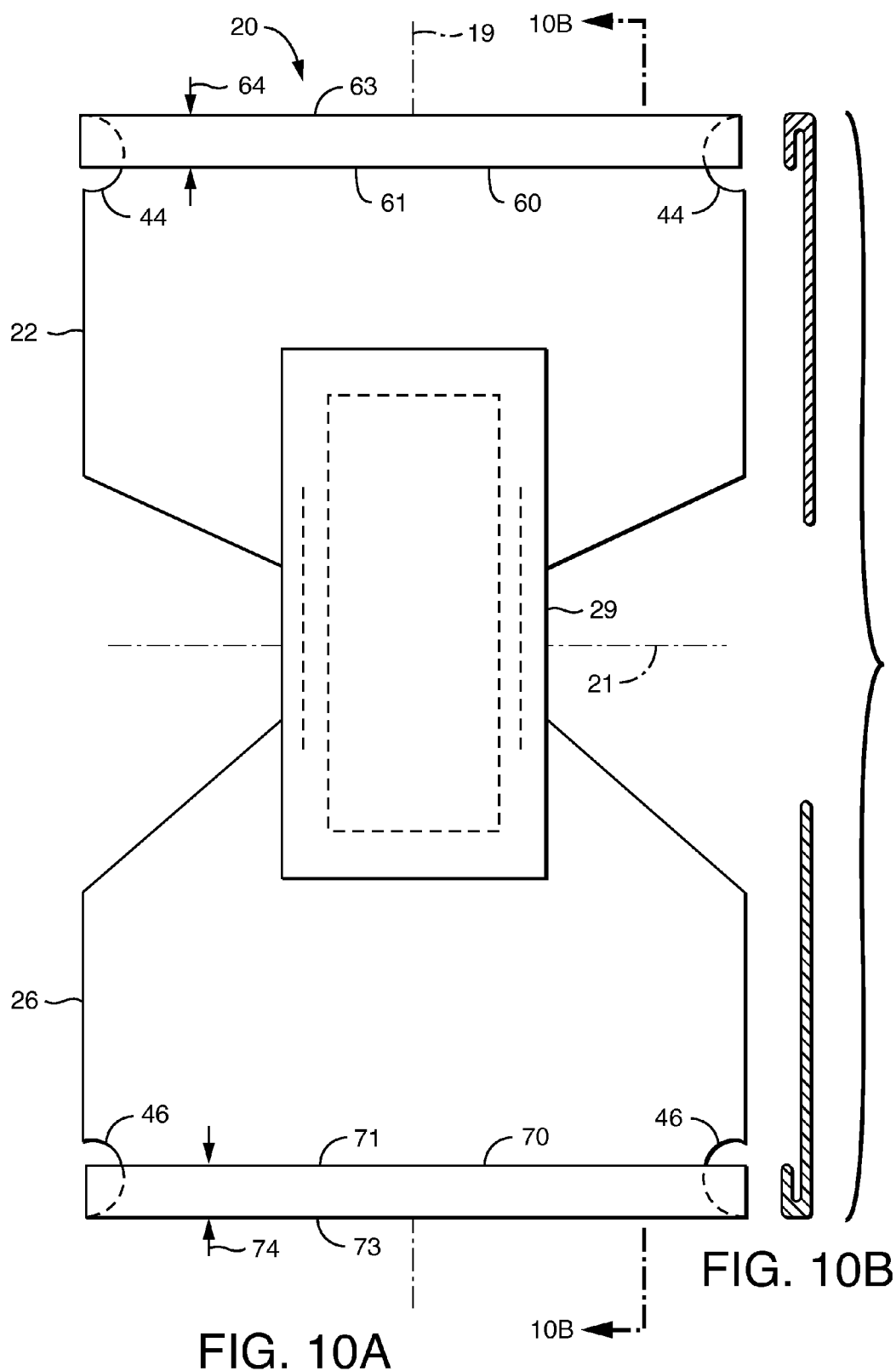
FIG. 10A representatively illustrates a plan view of an alternative embodiment of a disposable absorbent garment incorporating principles of the garment aspect of the present invention, shown in a fully stretched and laid-flat condition, prior to the joining of the front and back waist regions, and showing the surface of the article that faces toward the wearer when the article is worn.
FIG. 10B is a cross-sectional view of the article of FIG. 10A as viewed along line 10B-10B.
Figure 10C:
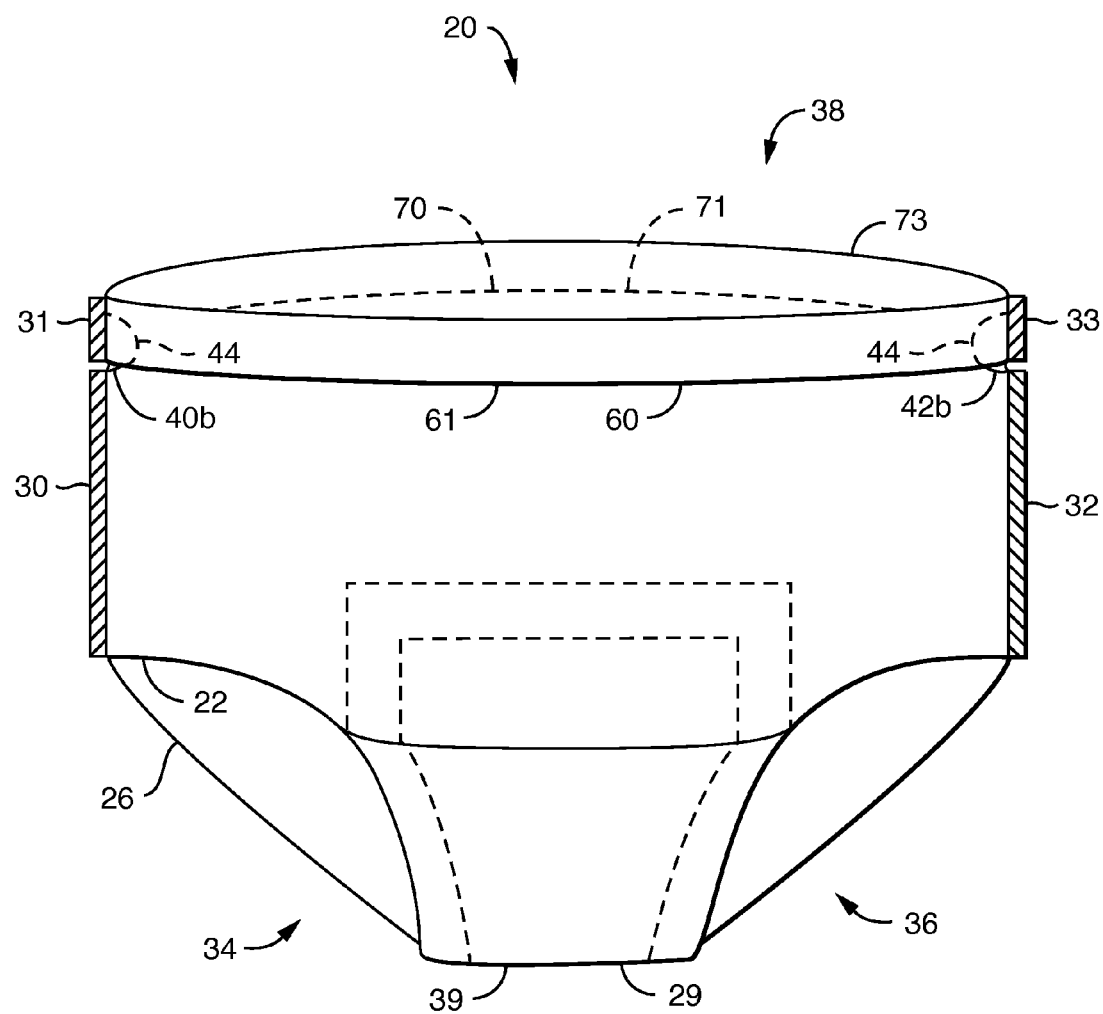
FIG. 10C is a front perspective view of the article of FIG. 10A, shown in a fully assembled condition.
Figure 10D:
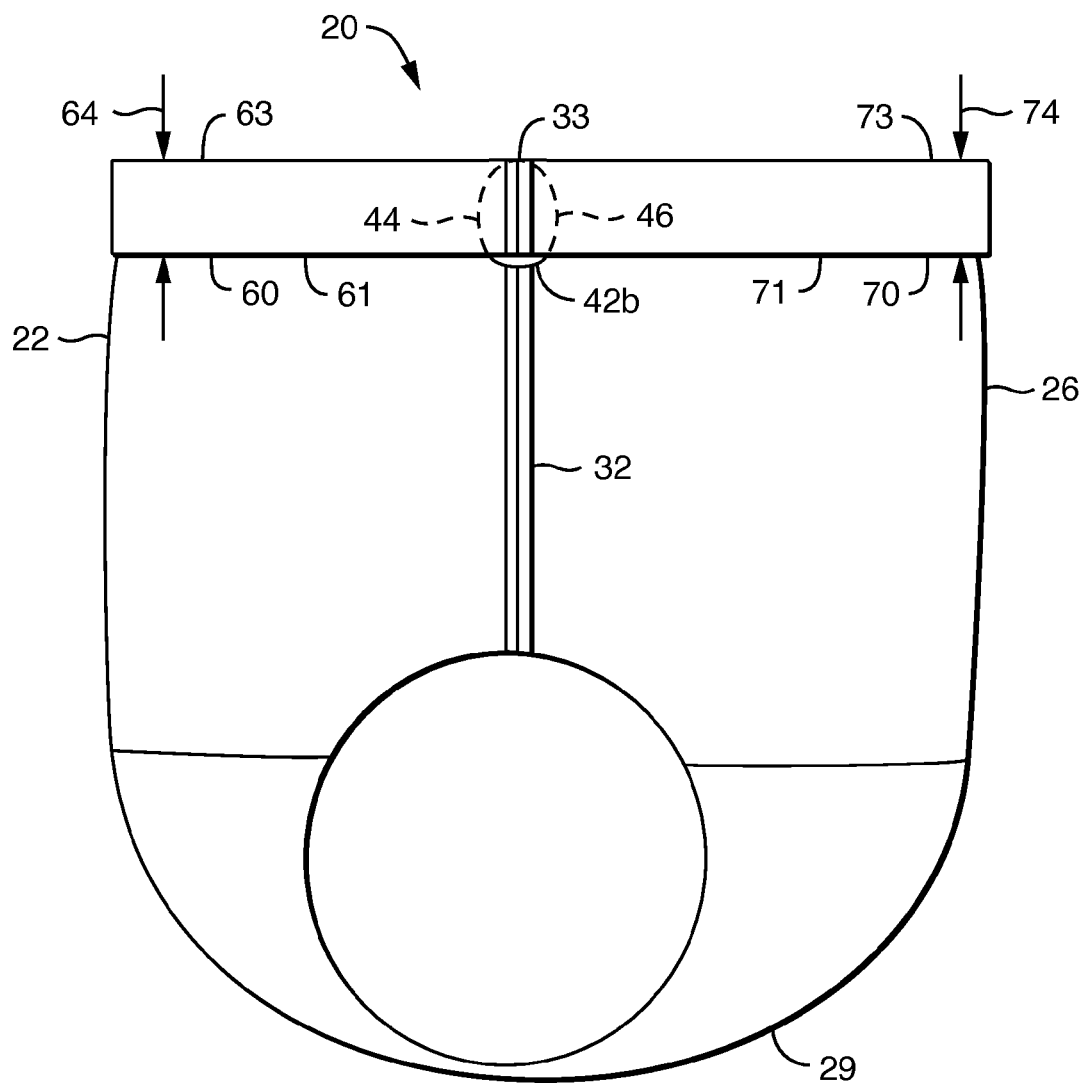
FIG. 10D is a side view of the article of FIG. 10C.
Figure 10G:
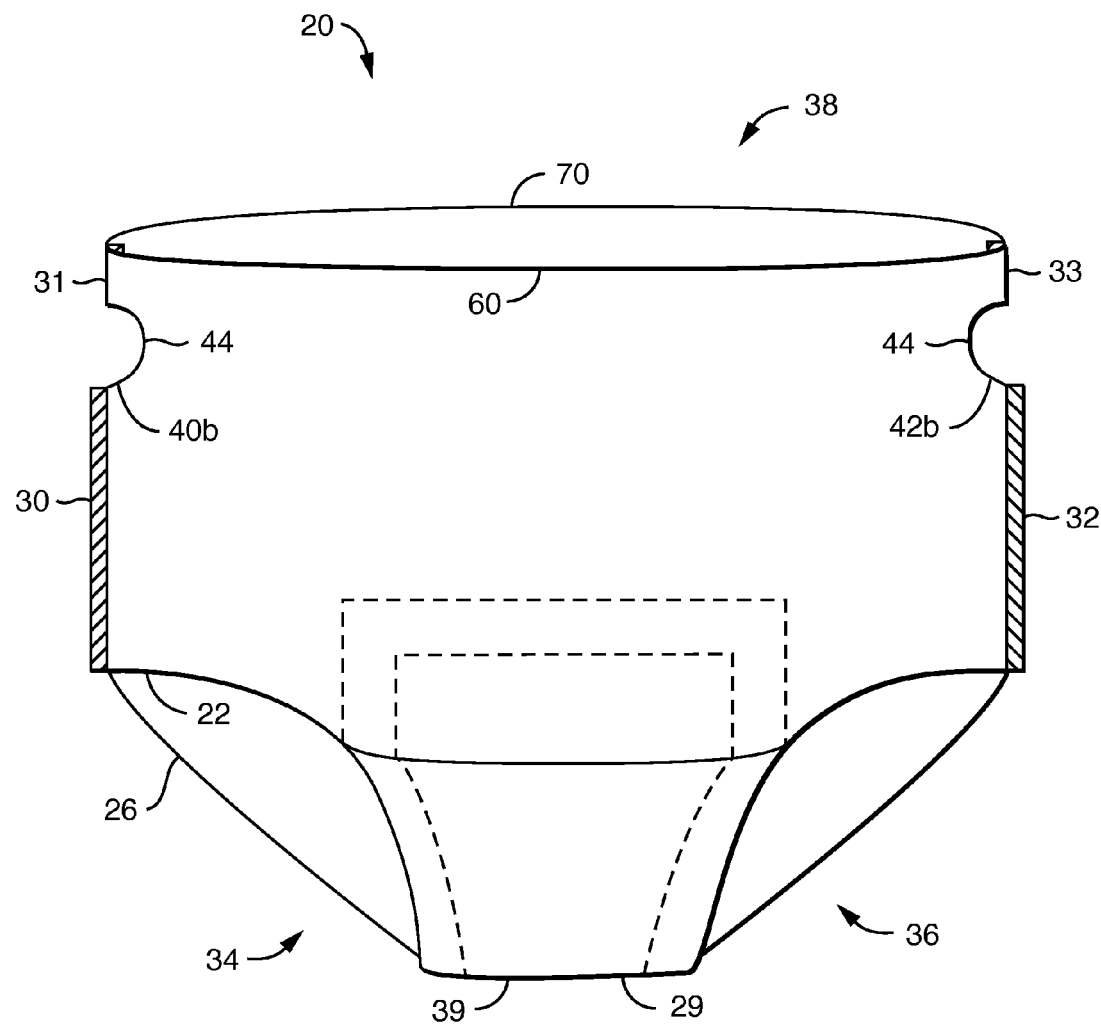
FIG. 10G is a front perspective view of the article of FIG. 10E, shown in a fully assembled condition.
Figure 10H:
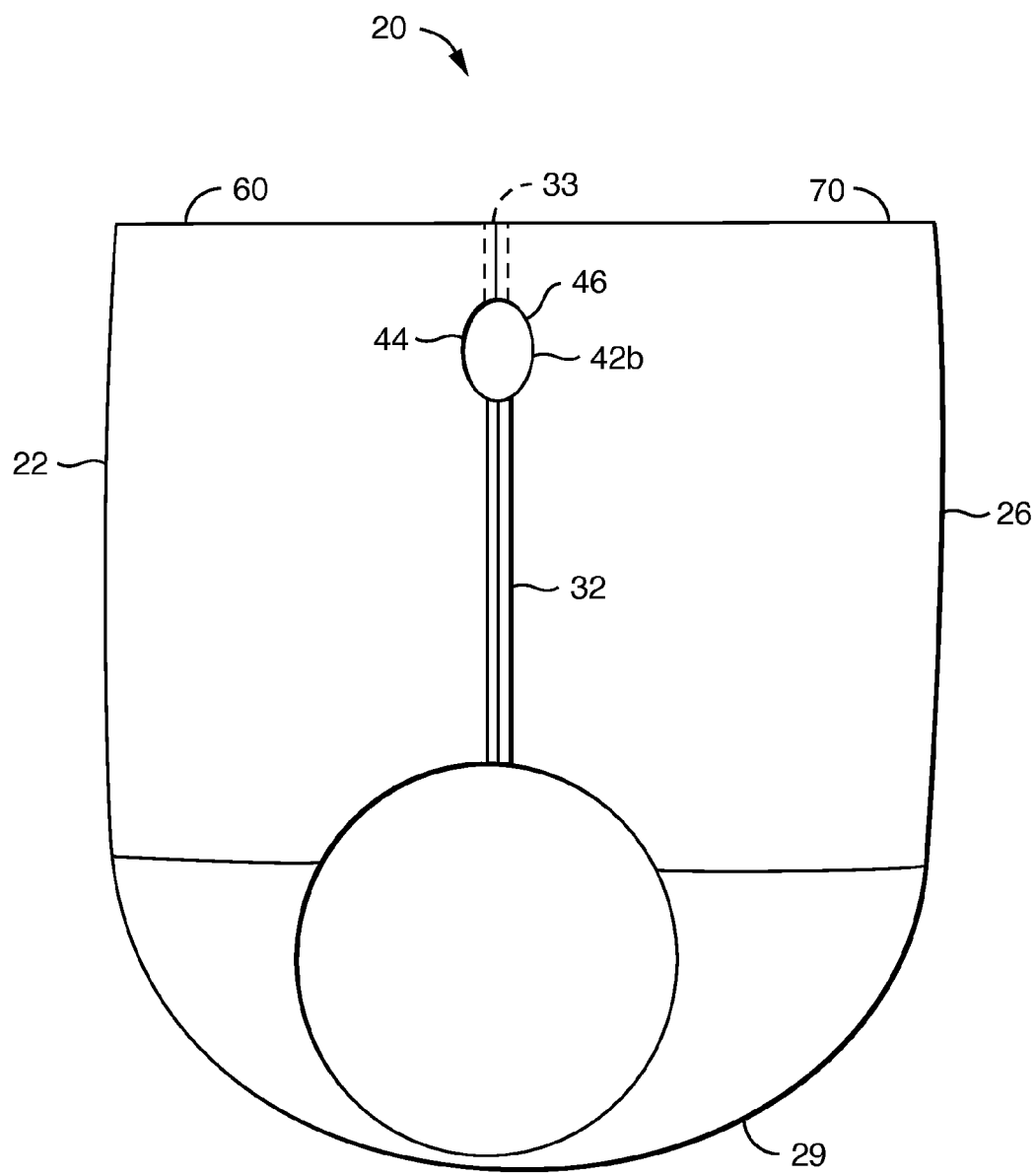
FIG. 10H is a side view of the article of FIG. 10G.

Still referring to FIGS. 5-8, the method 100 of this alternative approach further includes providing a front elastic waistband web 130 and a back elastic waistband web 140, such as via roll supplies 131 and 141 respectively. The method further includes positioning the front elastic waistband web 130 and the back elastic waistband web 140 in any of the manners described above with respect to the embodiments of FIGS. 1-4. For example, the waistband webs can be positioned to partially or completely cover the openings, whether holes or notches. Further, as above, separately provided waistband webs can be positioned such that distal edges 134/144 are substantially flush with, laterally outward of, or laterally inward of the respective waist edge 114/118. Further, as above, the waistband webs 130 and 140 may be substantially unattached to the front and back panel webs 113 and 117, respectively, along their respective proximal edges 133 and 143 in any of the manners described above with respect to the embodiments of FIGS. 1-4. As depicted in FIGS. 5-7, the waistband webs 130/140 may be distinct and separately provided from the front and back panel webs 113/117 (similar to the embodiments of FIGS. 1-3). Alternatively, as depicted in FIG. 8, the waistband webs 130/140 may be integral with and formed by folding the front and back panel webs 113/117 (similar to the embodiment of FIG. 4).

The method in this alternative configuration further includes providing a supply 150 of individual absorbent assemblies 50, each individual absorbent assembly 50 having a front end 51 and a back end 52. The absorbent assemblies can be configured and provided as described earlier. The method further includes attaching the front end 51 of each individual absorbent assembly 50 to the front panel web 113, and attaching the back end 52 of each individual absorbent assembly 50 to the back panel web 117 to create a composite garment web 190 such that each individual absorbent assembly 50 extends laterally between and interconnects the front panel web 113 to the back panel web 117.

The method in this embodiment further comprises folding the composite garment web 190 (such as at folding station 154) along a longitudinally extending centerline 104 that extends in the machine direction 102, such that the front waist edge 114 is brought into close proximity with the back waist edge 118. The method further includes attaching the front panel web 113 to the back panel web 117 (such as at seaming station 156) to create a series of garment side seam bonds 160 spaced apart in the machine direction 102. The method further includes attaching the front elastic waistband web 130 to the back elastic waistband web 140 (such as at seaming station 158) to create a series of waistband side seam bonds 162 spaced apart in the machine direction 102. Finally, the method includes cutting the composite garment web 190 and the elastic waistband webs 130/140 (such as at cutting station 168) at a series of cut locations 170 spaced apart in the machine direction 102 to create the plurality of disposable absorbent garments. The garment side seam bonds 160 and the waistband side seam bonds 162 can be made at the same seaming station (as depicted) or at separate seaming stations. Additionally, either or both of the seaming operations can be performed along with the final cutting operation at a single station, or at separate stations (as depicted).

Figure 2:
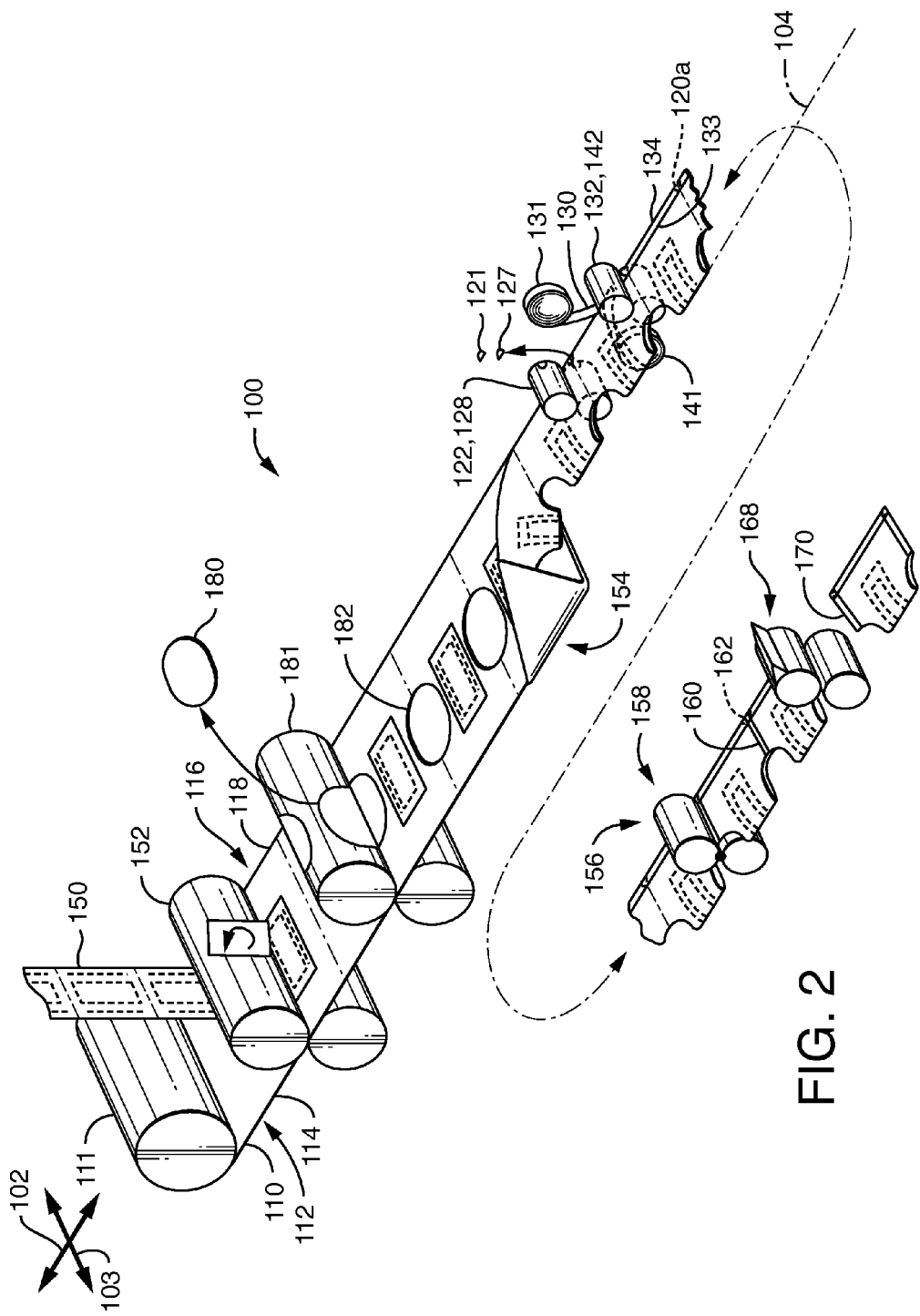
FIG. 2 representatively illustrates a perspective view of an alternative embodiment of a manufacturing process incorporating principles of the method aspect of the present invention.
Figure 3:
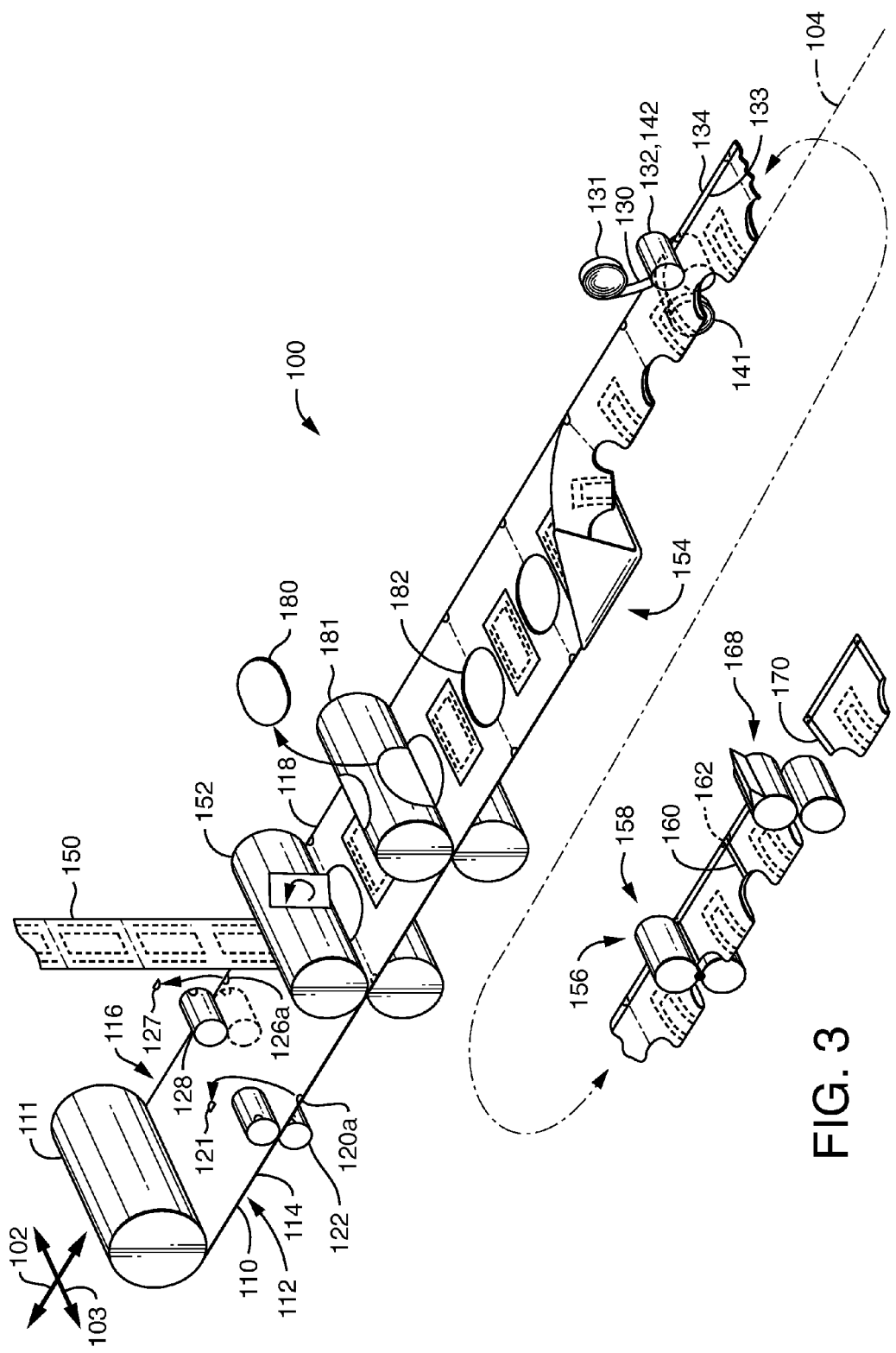
FIG. 3 representatively illustrates a perspective view of an alternative embodiment of a manufacturing process incorporating principles of the method aspect of the present invention.

The various stages of the method embodiments described above can be performed in a variety of orders. For example, in the embodiments depicted in FIGS. 1 and 5, the central portions 180 are removed and the garment web 110 (or composite garment web 190) is centrally folded after the openings 120/126 are formed and after the waistband webs 130/140 are introduced. In another example, as shown in the embodiments of FIGS. 2 and 6, the openings 120/126 are formed, and the waistband webs 130/140 applied, after the garment web 110 (or composite garment web 190) is centrally folded. In still another example, depicted in FIGS. 3 and 7, the openings 120/126 are formed before the garment web 110 (or composite garment web 190) is centrally folded, but the waistband webs 130/140 are applied after the garment web 110 (or composite garment web 190) is centrally folded. Other variations are possible, so long as the waistband webs 130/140 are introduced after the formation of the openings 120/126.

In another aspect, the present invention relates to a garment, such as, for example, a garment made by any of the above described method-of-manufacturing configurations. In one embodiment, the disposable absorbent garment 20 comprises a front panel 22 defining a front waist edge 24 and a back panel 26 defining a back waist edge 28. The garment further comprises a crotch panel 29 extending longitudinally between and connecting the front panel 22 and the back panel 26. The garment further comprises first and second transversely opposite side seams 30, 32 connecting the front panel 22 to the back panel 26, such that the garment defines first and second leg openings 34, 36 and a waist opening 38. As used in describing the various embodiments of the garment aspect of the present invention, the terms "longitudinal" and "transverse" have their customary meaning, as indicated by the longitudinal axis 19 and the transverse axis 21 depicted in FIGS. 9 and 10. The longitudinal axis 19 lies in the plane of the article when a fully stretched and laid-flat condition, prior to the joining of the front and back panels, and is generally parallel to a vertical plane that bisects a standing wearer into left and right body halves when the article is worn. The transverse axis 21 lies in the plane of the article generally perpendicular to the longitudinal axis 19.

The garment further includes first and second waist edge cutouts 40 and 42. In particular embodiments, the first side seam 30 extends from the first leg opening 34 to the first waist edge cutout 40, and the second side seam 32 extends from the second leg opening 36 to the second waist edge cutout 42. In particular embodiments, the cutouts 40 and 42 can be defined in part by a cutout segment 44 of the front panel 22 and in part by a cutout segment 46 of the back panel 26, as is the case in the exemplary embodiments of FIGS. 9 and 10. The cutouts 40 and 42 can be notches or holes, as defined earlier. For example, in one embodiment, an example of which is representatively illustrated in FIGS. 9A-9H, each first waist edge cutout 40 comprises a first waist edge notch 40a, and each second waist edge cutout 42 comprises a back waist edge notch 42a. In another embodiment, an example of which is representatively illustrated in FIGS. 10A-10H, each first waist edge cutout 40 comprises a first waist edge hole 40b, and each second waist edge cutout 42 comprises a second waist edge hole 42b.

The garment also includes a front elastic waistband 60 and a back elastic waistband 70. The front elastic waistband 60 is attached to the back elastic waistband 70 at first and second waistband side seams 31, 33. In particular embodiments, at least a portion of the first waistband side seam 31 overlays at least a portion of the first waist edge cutout 40, and at least a portion of the second waistband side seam 33 overlays at least a portion of the second waist edge cutout 42. "Overlay" as used in this context herein means that the waistband side seam is superposed over, or covers or partially covers, the cutout from a side view perspective, as depicted, for example, in FIGS. 9D and 10D. In particular embodiments, such as those representatively illustrated in FIGS. 9D and 10D, the entirety of the first waistband side seam 31 overlays the first waist edge cutout 40, and the entirety of the second waistband side seam 33 overlays the second waist edge cutout 42. The front elastic waistband 60 is attached to the front panel 22, such as via adhesive 66, and the back elastic waistband is attached to the back panel 26, such as via adhesive 76.

In certain embodiments, each front elastic waistband 60 defines a front waistband proximal edge 61 and a front waistband distal edge 62, the front waistband distal edge 62 being longitudinally outward of the front waistband proximal edge 61. "Longitudinally outward" as used to describe garment embodiments herein means in a direction longitudinally away from the central transverse axis 21 (if in a laid flat condition with the front and back panels unjoined to each other and the front and back waistbands unjoined to each other) or in a direction longitudinally from the crotch fold 39 to the waist opening 38 (if in a fully assembled condition). In particular embodiments of the garment, such as those representatively illustrated in FIGS. 9A-9D, the front waistband distal edge 62 is substantially flush (as defined above) with the front waist edge 24. In another embodiment, the front waistband distal edge 62 is positioned longitudinally outward of the front waist edge 24. In still another embodiment, the front waistband distal edge 62 is positioned longitudinally inward of the front waist edge 24. "Longitudinally inward" as used to describe garment embodiments herein means in a direction longitudinally toward the central transverse axis 21 (if in a laid flat condition with the front and back panels unjoined to each other and the front and back waistbands unjoined to each other) or in a direction longitudinally from the waist opening 38 toward the crotch fold 39 (if in a fully assembled condition). Similarly, each back elastic waistband 70 defines a back waistband proximal edge 71 and a back waistband distal edge 72, the back waistband distal edge 72 being longitudinally outward of the back waistband proximal edge 71. In particular embodiments of the garment, such as those representatively illustrated in FIGS. 9A-9D, the back waistband distal edge 72 is substantially flush (as defined above) with the back waist edge 28. In another embodiment, the back waistband distal edge 72 is positioned longitudinally outward of the back waist edge 28. In still another embodiment, the back waistband distal edge 72 is positioned longitudinally inward of the back waist edge 28.

In certain embodiments, as is representatively illustrated in FIGS. 10A-10H, the front elastic waistband is not a separately supplied element, but is instead integral with one or more of the panels, wherein the front elastic waistband 60 comprises a folded portion of the front panel 22, the folded portion of the front panel 22 defining a front end fold 63. Each such front elastic waistband 60 defines a front waistband proximal edge 61 positioned longitudinally inward of the front end fold 63. Similarly, in addition or in the alternative, the back elastic waistband 70 can comprise a folded portion of the back panel 26, the folded portion of the back panel 26 defining a back end fold 73. Each such back elastic waistband 70 defines a back waistband proximal edge 71 positioned longitudinally inward of the back end fold 73.

Referring to both FIGS. 9 and 10, in particular embodiments, the front waistband proximal edge 61 is substantially unattached to the front panel 22, and/or the back waistband proximal edge 71 is substantially unattached to the back panel 26. "Substantially unattached" as used herein to refer to garment embodiments means unattached along at least 90% of the transversely extending length of the waistband. This optional configuration, in which one or both of the front/back waistband proximal edges are unattached to the respective front/back panel, can provide improved donning of the garment by providing a lip under which a wearer can place his or her fingertips to assist in pulling up the underwear-like garment. Many users of incontinence garments, such as young children and elderly individuals, have difficulty pulling up pant-style products. By leaving the proximal edge of one or both of the front/back waistbands substantially unattached, users of the garment can, in certain embodiments of the present invention, use the proximal edge of the waistband as a handle to don the garment.

For example, as representatively illustrated in FIGS. 9 and 10, the front elastic waistband 60 defines a longitudinally extending width 64 which extends from the front waistband proximal edge 61 to the front waistband distal edge 62 (for non-integral waistbands as in FIG. 9), or from the front waistband proximal edge 61 to the front end fold 63 (for integral waistbands as in FIG. 10). In particular embodiments, the front elastic waistband 60 is substantially unattached to the front panel 22 along a majority, and more preferably along at least 75%, of the front elastic waistband width 64. Similarly, the back elastic waistband 70 defines a longitudinally extending width 74 which extends from the back waistband proximal edge 71 to the back waistband proximal edge 72 (for non-integral waistbands as in FIG. 9), or from the back waistband proximal edge 71 to the back end fold 73 (for integral waistbands as in FIG. 10). In particular embodiments, the back elastic waistband 70 is substantially unattached to the back panel 26 along a majority, and more preferably along at least 75%, of the back elastic waistband width 74. In addition, in embodiments employing separately attached, non-integral waistbands, the front waistband distal edge 62 can optionally be attached to the front panel 22 along the entirety of the transversely extending length 65 of the front elastic waistband 60, and/or the back waistband distal edge 72 can be attached to the back panel 26 along the entirety of the transversely extending length 75 of the back elastic waistband 70.

In particular embodiments of the garment aspect of the present invention, representatively illustrated in FIGS. 9 and 10, the front elastic waistband 60 and/or the back elastic waistband 70 is configured to be folded up and away from the respective front/back panel 22/26, such as after the garment has been pulled up around the wearer's waist. For example, as representatively illustrated in FIGS. 9E-H and 10E-H, the front waistband 60 and the back waistband 70 can be folded up (longitudinally outward). Such a configuration can enhance the underwear-like appearance of the garment, providing the waistband(s) with a more finished look, and increasing the rise of the pant which can be desirable in certain instances. Note that in the depicted embodiments, the waistband side seams 31/33 become inverted and appear on the inside of the waist opening 38 after the waistbands 60/70 are folded up.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of manufacturing a plurality of disposable absorbent garments comprising:
    providing a front panel web traveling in a machine direction, the front panel web defining a front waist edge extending in the machine direction;
    providing a back panel web traveling in the machine direction, the back panel web defining a back waist edge extending in the machine direction;
    removing portions of the front panel web adjacent to the front waist edge to define a series of spaced apart front waist edge openings;
    removing portions of the back panel web adjacent to the back waist edge to define a series of spaced apart back waist edge openings;
    providing a front elastic waistband web and a back elastic waistband web;
    positioning the front elastic waistband web proximate the front waist edge such that the front elastic waistband web overlays at least a portion of each front waist edge opening;
    positioning the back elastic waistband web proximate the back waist edge such that the back elastic waistband web overlays at least a portion of each back waist edge opening;
    providing a supply of individual absorbent assemblies, each individual absorbent assembly having a front end and a back end, and attaching the front end of each individual absorbent assembly to the front panel web and attaching the back end of each individual absorbent assembly to the back panel web to create a composite garment web such that each individual absorbent assembly extends laterally between and interconnects the front panel web to the back panel web;

folding the composite garment web along a central fold line that extends in the machine direction, such that the front waist edge is brought into close proximity with the back waist edge;

attaching the front panel web to the back panel web to create a series of garment side seam bonds spaced apart in the machine direction;

attaching the front elastic waistband web to the back elastic waistband web to create a series of waistband side seam bonds spaced apart in the machine direction; and cutting the garment web and the elastic waistband webs at a series of cut locations spaced apart in the machine direction to create the plurality of disposable absorbent garments.

2. The method of claim 1 wherein the front elastic waistband web is provided as a separate component distinct from the front panel web, and wherein the back elastic waistband web is provided as a separate component distinct from the back panel web.

3. The method of claim 1 wherein each front waist edge opening comprises a front waist edge notch, and each back waist edge opening comprises a back waist edge notch.

4. The method of claim 3 wherein each front elastic waistband web defines a front waistband web proximal edge and a front waistband web distal edge, the front waistband web distal edge being laterally outward of the front waistband web proximal edge, and wherein positioning the front elastic waistband web comprises positioning the front waistband web distal edge to be substantially flush with the front waist edge; and further wherein each back elastic waistband web defines a back waistband web proximal edge and a back waistband web distal edge, the back waistband web distal edge being laterally outward of the back waistband web proximal edge, and wherein positioning the back elastic waistband web comprises positioning the back waistband web distal edge to be substantially flush with the back waist edge.

5. The method of claim 2 wherein the front waistband web proximal edge is substantially unattached to the front panel web, and wherein the back waistband web proximal edge is substantially unattached to the back panel web.

6. The method of claim 5 wherein the front waistband web defines a laterally extending width, and wherein the front waistband web is substantially unattached to the front panel web in the longitudinal direction along a majority of said front waistband web width; and further wherein the back waistband web defines a laterally extending width, and wherein the front waistband web is substantially unattached to the back panel web in the longitudinal direction along a majority of said back waistband web width.

7. The method of claim 1 wherein the front elastic waistband web is integral with the front panel web and wherein the back elastic waistband web is integral with the back panel web, further wherein providing the front elastic waistband web comprises folding the front panel web laterally inward to define a front end fold, and wherein providing the back elastic waistband web comprises folding the back panel web laterally inward to define a back end fold.

8. The method of claim 7 wherein each front waist edge opening comprises a front waist edge hole, and each back waist edge opening comprises a back waist edge hole.

9. The method of claim 8 wherein each front elastic waistband web defines a front waistband web proximal edge positioned laterally inward of the front end fold, and wherein each back elastic waistband web defines a back waistband web proximal edge positioned laterally inward of the back end fold, further wherein the front waistband web proximal edge is substantially unattached to the front panel web, and wherein the back waistband web proximal edge is substantially unattached to the back panel web.

10. The method of claim 9 wherein the front waistband web defines a laterally extending width, and wherein the front waistband web is substantially unattached to the front panel web in the longitudinal direction along a majority of said front waistband web width; and further wherein the back waistband web defines a laterally extending width, and wherein the front waistband web is substantially unattached to the back panel web in the longitudinal direction along a majority of said back waistband web width.

11. The method of claim 1 further comprising positioning the front elastic waistband web such that the front elastic waistband web overlays an entirety of each front waist edge opening, and further comprising positioning the back elastic waistband web such that the back elastic waistband web overlays an entirety of each back waist edge opening.

12. The method of claim 1 wherein the front panel web is distinct from and spaced laterally apart from the back panel web.

13. The method of claim 1 further comprising providing a parent web, and slitting the parent web to provide the front panel web and the back panel web.

14. A disposable absorbent garment comprising:
a front panel defining a front waist edge and a back panel defining a back waist edge, the garment further comprising a crotch panel extending longitudinally between and connecting the front panel and the back panel, the garment further comprising first and second transversely opposite side seams connecting the front panel to the back panel, the garment further defining first and second leg openings and a waist opening;

first and second waist edge cutouts, wherein the first side seam extends from the first leg opening to the first waist edge cutout, and wherein the second side seam extends from the second leg opening to the second waist edge cutout;

a front elastic waistband and a back elastic waistband, wherein the front elastic waistband is attached to the back elastic waistband at first and second waistband side seams;

wherein at least a portion of the first waistband side seam overlays at least a portion of the first waist edge cutout, and wherein at least a portion of the second waistband side seam overlays at least a portion of the second waist edge cutout.

15. The garment of claim 14 wherein each first waist edge cutout comprises a first waist edge notch, and each second waist edge cutout comprises a second waist edge notch.

16. The garment of claim 15 wherein each front elastic waistband defines a front waistband proximal edge and a front waistband distal edge, the front waistband distal edge being longitudinally outward of the front waistband proximal edge, and wherein the front waistband distal edge is substantially flush with the front waist edge, and further wherein each back elastic waistband defines a back waistband proximal edge and a back waistband distal edge, the back waistband distal edge being longitudinally outward of the back waistband proximal edge, and wherein the back waistband distal edge is substantially flush with the back waist edge.

17. The garment of claim 14 wherein the front waistband proximal edge is substantially unattached to the garment web, and wherein the back waistband proximal edge is substantially unattached to the garment web.

18. The garment of claim 17 wherein the front elastic waistband defines a longitudinally extending width, and wherein the front elastic waistband is substantially unattached to the front panel along a majority of said front elastic waistband width; and further wherein the back elastic waistband defines a longitudinally extending width, and wherein the back elastic waistband is substantially unattached to the back panel along a majority of said back elastic waistband width.

19. The garment of claim 14 wherein the front elastic waistband comprises a folded portion of the front panel, the folded portion of the front panel defining a front end fold, and wherein the back elastic waistband comprises a folded portion of the back panel, the folded portion of the back panel defining a back end fold.

20. The garment of claim 19 wherein each first waist edge cutout comprises a first waist edge hole, and each second waist edge cutout comprises a second waist edge hole.

21. The garment of claim 20 wherein each front elastic waistband defines a front waistband proximal edge positioned longitudinally inward of the front end fold, and wherein each back elastic waistband defines a back waistband proximal edge positioned longitudinally inward of the back end fold, further wherein the front waistband proximal edge is substantially unattached to the front panel, and wherein the back waistband proximal edge is substantially unattached to the back panel.

22. The garment of claim 21 wherein the front elastic waistband defines a longitudinally extending width, and wherein the front elastic waistband is substantially unattached to the front panel along a majority of said front elastic waistband width; and further wherein the back elastic waistband defines a longitudinally extending width, and wherein the front elastic waistband is substantially unattached to the back panel along a majority of said back elastic waistband width.

23. The garment of claim 14 wherein the entirety of the first waistband side seam overlays the first waist edge cutout, and wherein the entirety of the second waistband side seam overlays the second waist edge cutout.

* * * * *